US007871796B2

(12) United States Patent
Chen et al.

(10) Patent No.: US 7,871,796 B2
(45) Date of Patent: Jan. 18, 2011

(54) ISOLATION OF BINDING PROTEINS WITH HIGH AFFINITY TO LIGANDS

(75) Inventors: Gang Chen, Austin, TX (US); Andrew Hayhurst, Austin, TX (US); Jeffrey G. Thomas, Bellevue, WA (US); Brent L. Iverson, Austin, TX (US); George Georgiou, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1102 days.

(21) Appl. No.: 11/461,757

(22) Filed: Aug. 1, 2006

(65) Prior Publication Data

US 2007/0065913 A1 Mar. 22, 2007

Related U.S. Application Data

(62) Division of application No. 09/699,023, filed on Oct. 27, 2000, now Pat. No. 7,083,945.

(51) Int. Cl.
*C12P 21/06* (2006.01)
*C07H 21/04* (2006.01)
(52) U.S. Cl. ............................ 435/69.1; 435/4; 435/183
(58) Field of Classification Search ........................ None
See application file for complete search history.

(56) References Cited

U.S. PATENT DOCUMENTS 5,160,974 A 11/1992 Siegel et al. ................ 356/246

5,223,409 A 6/1993 Ladner et al. .............. 435/69.7

(Continued)

FOREIGN PATENT DOCUMENTS

EP 177343 4/1986

(Continued)

OTHER PUBLICATIONS

Streeter, John G. Journal of General Microbiology, 1989, vol. 135, pp. 3477-3484, Analysis of Periplasmic Enzymes in Intact Cultured Bacteria and Bacteroids of *Bradyrhizobium japonicum* and Rhizobium leguminosarum biovar phaseoli.*

(Continued)

*Primary Examiner*—Mark Navarro
*Assistant Examiner*—Ginny Portner
(74) *Attorney, Agent, or Firm*—Fulbright & Jaworski L.L.P.

(57) ABSTRACT

The invention overcomes the deficiencies of the prior art by providing a rapid approach for isolating binding proteins capable of binding small molecules and peptides via "display-less" library screening. In the technique, libraries of candidate binding proteins, such as antibody sequences, are expressed in soluble form in the periplasmic space of gram negative bacteria, such as *Escherichia coli*, and are mixed with a labeled ligand. In clones expressing recombinant polypeptides with affinity for the ligand, the concentration of the labeled ligand bound to the binding protein is increased and allows the cells to be isolated from the rest of the library. Where fluorescent labeling of the target ligand is used, cells may be isolated by fluorescence activated cell sorting (FACS). The approach is more rapid than prior art methods and avoids problems associated with the surface-expression of ligand fusion proteins employed with phage display.

41 Claims, 10 Drawing Sheets

U.S. PATENT DOCUMENTS

| | | | |
|---|---|---|---|
| 5,348,867 A | 9/1994 | Georgiou et al. | 435/69.7 |
| 5,571,698 A | 11/1996 | Ladner et al. | 435/69.7 |
| 5,648,237 A | 7/1997 | Carter | 435/69.1 |
| 5,656,015 A | 8/1997 | Young | 601/2 |
| 5,744,314 A | 4/1998 | Menzel et al. | 435/7.2 |
| 5,759,810 A | 6/1998 | Honjo et al. | 435/69.1 |
| 5,780,279 A | 7/1998 | Matthews et al. | 435/172.3 |
| 5,824,520 A | 10/1998 | Mulligan-Kehoe | 435/91.41 |
| 5,837,500 A | 11/1998 | Ladner et al. | 435/69.7 |
| 5,866,344 A | 2/1999 | Georgiou | 435/7.21 |
| 5,871,907 A * | 2/1999 | Winter et al. | 506/9 |
| 5,922,545 A | 7/1999 | Mattheakis et al. | 435/6 |
| 5,955,604 A * | 9/1999 | Tsien et al. | 540/222 |
| 6,001,823 A | 12/1999 | Hultgren et al. | 514/99 |
| 6,004,940 A * | 12/1999 | Marasco et al. | 514/44 A |
| 6,248,904 B1 * | 6/2001 | Zhang et al. | 549/227 |
| 6,335,178 B1 * | 1/2002 | Weiner et al. | 435/69.1 |
| 6,335,198 B1 * | 1/2002 | delCardayre et al. | 435/440 |
| 6,335,429 B1 * | 1/2002 | Cai et al. | 530/402 |
| 6,342,611 B1 * | 1/2002 | Weber et al. | 549/227 |
| 6,352,859 B1 * | 3/2002 | delCardayre et al. | 435/400 |
| 6,379,964 B1 * | 4/2002 | del Cardayre et al. | 435/440 |
| 6,528,311 B1 * | 3/2003 | delCardayre et al. | 435/440 |
| 6,548,249 B1 * | 4/2003 | Anderson et al. | 506/10 |
| 6,548,632 B1 * | 4/2003 | Anderson et al. | 506/18 |
| 6,562,617 B1 * | 5/2003 | Anderson et al. | 506/14 |
| 6,716,631 B1 * | 4/2004 | delCardayre et al. | 435/440 |
| 6,916,474 B2 | 7/2005 | Harvey et al. | 424/130.1 |
| 7,033,781 B1 * | 4/2006 | Short | 435/69.1 |
| 7,083,945 B1 * | 8/2006 | Chen et al. | 435/69.1 |
| 7,094,571 B2 * | 8/2006 | Harvey et al. | 435/69.1 |
| 7,611,866 B2 * | 11/2009 | Georgiou et al. | 435/69.1 |
| 2002/0090666 A1 * | 7/2002 | Fritz et al. | 435/23 |
| 2005/0260736 A1 | 11/2005 | Georgiou et al. | 435/252.3 |
| 2006/0029947 A1 | 2/2006 | Georgiou et al. | 435/6 |
| 2007/0099267 A1 | 5/2007 | Harvey et al. | 435/69.1 |

FOREIGN PATENT DOCUMENTS

| | | |
|---|---|---|
| WO | WO 98/49286 | 11/1998 |
| WO | WO 99/60096 | 11/1999 |
| WO | WO 02/22861 | 3/2002 |
| WO | WO 02/34886 | 5/2002 |
| WO | WO 2005/019409 | 3/2005 |
| WO | WO 2005/095988 | 10/2005 |

OTHER PUBLICATIONS

Swiss-Prot Accession No. C6B352.*
Martinez, Michael B et al, Biochemistry, vol. 35, 1996, pp. 1179-1186, Accurate Kinetic Modeling of Alkaline Phosphatase in the *Escherichia coli* Periplasm: Implication sfor Enzyme Properties and Substrate Diffusion.*
Swiss-Prot Accession No. P00634.*
Ames, *J. Bioenergetics and Biomembranes*, 20:1-17, 1988.
Boder and Wittrup, "Yeast surface display for screening combinatorial polypeptide libraries," *Nature Biotechnology*, 15:553-557, 1997.
Boeke et al, "Effects of Bacteriophage f1 Gene III Protein on the Host Cell Membrane," *Mol. Gen. Genet.*, 186:185-192, 1982.
Bradbury, "Selecting by microdialysis," *Nature Biotechnology*, 19:528-529, 2001.
Buchner and Rudolph, "Renaturation, purification, and characterization of recombinant Fab-fragments produced in *Escherichia coli*," *Enzyme Microb. Technol*, 9(2):157-162, 1991.
Bukau et al., *J Bacteriology*, 163:61-68, 1985.
Burioni et al., "A new subtraction technique for molecular cloning of rare antiviral antibody specificities from phage display libraries," *Res. Virol.*, 149:327-330, 1998.
Burman et al., "Murein and the Outer Penetration Barrier of *Escherichia coli* K-12, *Proteus mirabilis*, and *Pseudomonas aeruginosa*,"*J Bacteriol.*, 112(3):1364-1374, 1972.

Chen et al., "Isolation of high-affinity ligand-binding proteins by periplasmic expression with cytometric screening (PECS)," *Nature Biotechnology*, 19:537-542, 2001.
Chowdhury and Pastan, "Improving antibody affinity by mimicking somatic hypermutation in vitro," *Nat. Biotech.*, 17:568-572, 1999.
Coia et al., "Use of mutator cells as a means for increasing production levels of a recombinant antibody directed against Hepatitis B," *Gene* 201:203-209, 1997.
Dall'Acqua and Carter, "Antibody engineering," *Curr. Opin. Struct. Biol.*, 8:443-450, 1998.
Danese and Silhavy, "Targeting and assembly of periplasmic and outer-membrane proteins in *Escherichia coli*," *Annu. Rev. Genet.*, 32:59-94, 1998.
Daugherty et al., "Development of an optimized expression system for the screening of antibody libraries displayed on the *Escherichia coli* surface," Prot. Eng., 12:613-620, 1999.
Daugherty et al., "Flow cytometric screening of cell-based libraries," *J Immunol. Methods*. 243:211-227, 2000.
De Haard A et al., "A Large Non-immunized Human Fab Fragment Phage Library That Permits Rapid Isolation and Kinetic Analysis of High Affinity Antibodies," *J. Biol. Chem.*, 274:18218-18230, 1999.
De Wildt et al., "Antibody arrays for high-throughput screening of antibody—antigen interactions,"*Nat. Biotechnol.* 18:989-994, 2000.
Decad and Nikaido, "Outer Membrane of Gram-Negative Bacteria, XII Molecular-Sieving Function of Cell Wall," *J. Bacteriol*, 128:325-336, 1976.
Deng et al., "Basis for selection of improved carbohydrate-binding single-chain antibodies from synthetic gene libraries," *Proc. Natl. Acad. Sci. USA*. 92:4992-4996, 1995.
Deng et al., "Selection of Antibody Single-chain Variable Fragments with Improved Carbohydrate Binding by Phage Display," *J Biol. Chem.*, 269:9533-9538, 1994.
Duenas and Borrebaeck, "Clonal selection and Amplification of Phage Displayed Antibodies by Linking Antigen Recognition and Phage Replication," *Biotechnology*, 12:999-1002, 1994.
Farmer et al., "Penetration of β-lactamase inhibitors into the periplasm of Gram-negative bacteria," *FEMS Microbial. Lett.*, 176:11-15, 1999.
Feilmeier et al., "Green fluorescent protein functions as a reporter for protein localization in *Escherichia coli*," *J. Bacteriol*, 182:4068-4076, 2000.
Georgiou and Valax, "Expression of correctly folded proteins in *Esherichia coli*," *Curr. Opin. Biotechnol.*, 7:190-197, 1996.
Georgiou et al., "Display of heterologous proteins on the surface of microorganisms: From the screening of combinatorial libraries to live recombinant vaccines," *Nat. Biotechnol.* 15:29-34, 1997.
Griep et al., "pSKAP/S: An Expression Vector for the Production of Single-Chain Fv Alkaline Phosphatase Fusion Proteins," *Prot. Exp. Purif.*, 16:63-69, 1999.
Griffiths et al., "Isolation of high affinity human antibodies directly formlarge synthetic repertoires," *EMBO J.*, 13: 3245-3260, 1994.
Hancock and Wong, "Compounds which increase the permeability of the Pseudomonas aeruginosa outer membrane," *Antimicrobial Agents and Chemotherapy*, 26:48-52, 1984.
Hawkins et al., "Selection of Phage Antibodies by Binding Affinity," *J Mol. Biol.*, 226:889-896, 1992.
Helander and Mattila-Sandholm, "Fluorometric assessment of gram-negative bacterial permeabilization," *J. of Applied Microbiology*, 88:213-219, 2000.
Higgins et al., "Binding protein-dependent transport systems," *J. Bioenergetics and Biomembranes*, 22:571-592, 1990.
Hobot et al., "Periplasmic Gel: New Concept Resulting from the Reinvestigation of Bacterial Cell Envelope Ultrastructure by New Methods," *J. Bacteriol*, 160(1):143-152, 1984.
Hoischen et al., "Novel bacterial membrane surface display system using cell wall-less L-forms of Proteus mirabilis and *Escherichia coli*," *Applied and Environmental Microbiology*, 68:525-531, 2002.
Hoogenboom et al., "Creating and engineering human antibodies from immunotherapy," *Adv. Drug. Deliv. Rev.*, 31:5, 1998.
Hoogenboom, "Designing and optimizing library selection strategies for generating high-affinity antibodies," *TIBTECH*, 15:62-70, 1997.
Hudson, "Recombinant antibody fragments," *Curr. Opin. Biotechnol.*, 9:395-402, 1998.

Johns et al., "In vivo selection of sFv from phage display libraries," *J. Immunol. Methods*, 239:137-151, 2000.

Joo et al., "A high-throughput digital imaging screen for the discovery and directed evolution of oxygenases," *Chemistry & Biology*, 6:699-706, 1999.

Jouenne and Junter, "Do β-lactam antibiotics permeabilize the outer membrane of Gram-negative bacteria? An electochemical investigation," *FEMS Microbiol. Lett.*, 68:313-318, 1990.

Kipriyanov et al., "Rapid detection of recombinant antibody fragments directed against cell surface antigens by flow cytometry," *J. Immunal. Methods*, 196:51-62, 1996.

Kjaer et al., "Glycerol diversifies phage repertoire selections and lowers non-specific phage absorption," *FEBS Lett.*, 431:448-452, 1998.

Knappick et al., "Fully Synthetic Human Combinatorial Antibody Libraries (HuCAL) Based on Modular Consensus Frameworks and CDRs Randomized with Trinucleotides," *J. Mol. Biol.*, 296:57-86, 2000.

Krebber et al., "Inclusion of an upstream transcriptional terminator in phage display vectors abolishes background expression of toxic fusions with coat protein g3p," *Gene*, 178:71-74, 1996.

Krebber et al., "Reliable cloning of functional antibody variable domains from hybridomas and spleen cell repertoires employing a reengineered phage display system," *J. Immunol. Methods*, 201:35-55, 1997.

Le and Trotta, "Purification of secreted recombinant proteins from *Escherichia coli*," *Bioprocess Technol.*, 12:163-181, 1991.

Levitan, "Stochastic Modeling and Optimization of Phage Display," *J. Mol. Biol.*, 277:893-916, 1998.

MacKenzie and To, "The role of valency in the selection of anti-carbohydrate singl-chain Fvs from phage display libraries," *J. Immunol. Methods*, 220:39-49, 1998.

MacKenzie et al, "Analysis by Surface Plasmon Resonance of the Influence of Valence on the Ligand Binding Affinity and Kinetics of an Anti-carbohydrate Antibody," *J. Biol. Chem.*, 271(3):1527-1533, 1996.

Makrides, "Strategies for achieving high-level expression of genes in *Escherichia coli*," *Microbiol. Rev.*, 60:512-538, 1996.

Malmborg et al., "Selection of binders from phage displayed antibody libraries using the BIAcore biosensor," *J. Immunol. Methods*, 198:51-57, 1996.

Martinez et al., "Accurate Kinetic Modeling of Alkaline Phosphatase in the *Escherichia coli* Periplasm: Implications for Enzyme Properitres and Substrate Diffusion," *Biochemistry*, 35:1179-1186, 1996.

Martinez et al., "Steady-state enzyme kinetics in the *Escherichia coli* periplasm: a model of a whole cell biocatalyst, " *J. Biotechnol.*, 71:59-66, 1999.

Maynard and Georgiou, "Antibody Engineering," *Annu. Rev. Biomed. Eng.*, 2:339-376, 2000.

Mutuberria et al., "Model systems to study the parameters determining the success of phage antibody selections on complex antigens," *J. Immunol. Methods*, 231:65-81, 1999.

Naglak and Wang, "Recovery of a foreign protein from the periplasm of *Escherichia coli* by chemical permeabilization," *Enzyme Microb. Technol.*, 12:603-611, 1990.

Nakae et al., *J. Bio. Chem.*, 250:7359-7365, 1975.

Nikaido and Vaara, "Molecular Basis of Bacterial Outer Membrane Permeability," *Microbiol. Rev.*, 49:1-32, 1985.

Oliver, "Periplasm," In: *Escherichia coil and Salmonella Cellular and Molecular Biology*, 88-103, 1996.

Olsen et al., "Function-based isolation of novel enzymes from a large library," *Nat. Biotechnol.*, 18:1071-1074, 2000.

Pini et al., "Design and Use of a Phage Display Library," *J. Biol. Chem.*, 273:21769-21776, 1998.

Pugsley, "The complete general secretary pathway in gram-negative bacteria," *Microbiol. Rev.*, 57:50-108, 1993.

Rodi and Makowski, "Phage-display technology—finding a needle in a vast molecular haystack," *Curr. Opin. Biotechnol.*, 10:87-93, 1999.

Sawyer and Blattner, "Rapid detection of antigen binding by antibody fragments expressed in the periplasm of *Escherichia coli*," *Protein Engineering*, 4:947-953, 1991.

Sblattero and Bradbury, "Exploiting recombination in single bacteria to make large phage antibody libraries," *Nat. Biotechnol.*, 18:75-80, 2000.

Sheets et al., "Efficient construction of a large nonimmune phage antibody library: The production of high-affinity human single-chain antibodies to protein antigens," *Proc. Natl. Acad. Sci. USA.*, 95:6157-6162, 1998.

Shusta et al., "Yeast Polypeptide Fusion Surface Display Levels Predict Thermal Stability and Soluble Secretion Efficiency," *J. Mol. Biol.*, 292:949-956, 1999.

Thompson et al., "Affinity Maturation of High-affinity Human Monoclonal Antibody Against the Third Hypervariable Loop of Human Immunodeficiency Virus: Use of Phage Display to Improve Affinity and Broaden Strain Reactivity," *J. Mol. Biol.* 256:77-88, 1999.

Van Wielink and Duine, "How big is the periplasmic space?" *Trends Biochem Sci.*, 15:136-137, 1990.

Vaughan et al., "Human Antibodies with Sub-nanomolar Affinities Isolated from a Large Non-immunized Phage Display Library," *Nat. Biotechnol.*, 14:309-314, 1996.

Webster's Ninth New Collegiate Dictionary, p. 354, 1990.

Wolfing and Pluckthun, "Protein folding in the periplasm of *Escherichia coli*," 12:685-692, 1994.

Barbas et al., "Assembly of combinatorial antibody libraries on phage surfaces: the gene III site," *Proc. Natl. Acad. Sci. USA*, 88:7978-7982, 1991.

Boder and Wittrup, "Yeast Surface Display for directed evolution of protein expression, affinity, and stability," *Methods Enzymol.*, 328:430-444, 2000.

Boder et al., "Directed evolution of antibody fragments with monovalent femtomolar antigen-binding affinity," *Proc. Natl. Acad. Sci. USA*, 97(20):10701-10705, 2000.

U.S. Appl. No. 10/288,269, filed Nov. 5, 2002, Georgiou et al.

Chen et al., "In vitro scanning saturation mutagenesis of all the specificity determining residues in an antibody binding site," *Protein Eng.*, 12(4):349-356, 1999.

Chen et al., "Selection and analysis of an optimized anti-VEGF antibody: crystal structure of an affinity-matured Fab in complex with antigen," *J. Mol. Biol.*, 293:865, 1999.

Cirino et al., "Disruption of anthrax toxin binding with the use of human antibodies and competitive inhibitors," *Infect. Immunity*, 67:2957-2963, 1999.

Corey et al., "Trypsin display on the surface of bacteriophage," *Gene*, 128:129-134, 1993.

Creighton, Thomas E., in his book "Protein Structure: A Practical Approach. 1989; pp. 184-186".

Creighton, Thomas E., in his book, "Proteins: Structures and Molecular Properties, 1984", (p. 315).

Daugherty et al., "Quantitative analysis of the effects of the mutation frequency on the affinity maturation of single chain Fc antibodies," *PNAS*, 97:2029-2034, 2000.

De Haard et al., "Creating and engineering human antibodies for immunotherapy," *Advanced Drug Delivery Reviews*, 31:5-31, 1998.

Fromant et al., "Direct random mutagenesis of gene-sized DNA fragments using polymerase chain reaction," *Anal. Biochem.*, 224:347-353, 1995.

Fuchs et al. "Seperation of *E. coli* expressing functional cell-wall bound antibody fragments by FACS," *Immunotechnology*, 2(2):97-102, 1996.

Georgiou, "Analysis of large libraries of protein mutants using flow cytometry," *Adv. Protein Chem.*, 55:293-315, 2000.

Gouffi et al., "Topology determination and functional analysis of the *Escherichia coli* TatC protein." *FEBS Lett.*, 525:65-70, 2002.

Harvey et al., "Anchored periplasmic expression, a versatile technology for the isolation of high-affinity antibodies from *Escherichia coli*-expressed libraries," *Proc. Natl. Acad. Sci., USA*, 101(25):9193-9198, 2004.

Harvey, "Anchored periplasmic expression (APEX) of protein libraries for flow cytometric selections," *American Chemical Society: Abstracts of paper at the national meeting of the American Chemical Society*, 224(1/2):BIOT-324, 2002.

Hayhurst and Georgiou, "High-throughput antibody isolation," *Curr. Opin. Chem. Biol.*, 5:683-689, 2001.

Hayhurst and Harris, "*Escherichia coli* Skp chaperone coexpression inproves solubility and phage display of single-chain antibody fragments." *Protein Expr. Purif.*, 15:336-343, 1999.

Hayhurst et al., "Isolation and expression of recombinant antibody fragments to the biological warfare pathogen *Brucella melitensis*," *J. Immunol. Methods*, 276:185-196, 2003.

Hayhurst, "Improved expression characteristics of single-chain Fv fragments when dowstream of the *Escherichia coli* maltose-binding protein or upstream of a single immunoglobulin-constant domain," *Protein Expr. Purif.*, 18:1-10, 2000.

Hoess, "Protein design and phage display," *Chem. Rev.*, 101:3205-3218, 2001.

Hultgren et al., "Bacterial adhesins and their assembly," In: *Escherichia coli and Salmonella Typhimurium. Cellular and Molecular Biology*, Frederick Neidhardt et al., eds. vol. 2:2730-2756, 1996.

Hultgren et al., "Pilus and nonpilus bacterial adhesins: assembly and function in cell recognition," *Cell*, 73:887-901, 1993.

Li et al., "X-ray snapshots of the maturation of an antibody response to protein antigen," *Nat. Struct. Biol.*, 10:482-488, 2003.

Low et al., "Mimicking somatic hypermutation: affinity maturation of antibodies displayed on bacteriophage using a bacterial mutator strain," *J. Mol. Biol.*, 260: 359-368, 1996.

Lutz et al., "Rapid generation of incremental truncation libraries for protein engineering using alpha-phosphothioate nucleotides." *Nucleic Acids Res.*, 29:E16, 2001.

Maenaka et al., "A stable phage-display system using a phagemid vector: phage display of hen egg-white lysozyme (HEL), *Escherichia coli* alkaline, phosphatase, and anti-HEL monoclonal antibody, HyHEL10," *Biochem. Biophys. Res. Commun.*, 218:682, 1996.

Maynard et al., "Protection against anthrax toxin by recombinant antibody fragments correlates with antigen affinity," *Nat. Biotechnol.*, 20:597-601, 2002.

Mingarro et al., "Membrane-protein engineering," *Trends Biotechnol.*, 15:432-437, 1997.

Miroux and Walker, "Over-production of proteins in *Escherichia coli*: mutant hosts that allow synthesis of some membrane proteins and globular proteins at high levels," *J. Mol. Biol.*, 260:289-298, 1996.

Nikaido, "Multidrug efflux pumps of gram-negative bacteria," *Journal of Bacteriology*, 178(20):5853-5859, 1996.

Nosoh et al. in "Protein stability and stabilization through protein engineering, 1991," (Chapter 7, p. 197).

Painbeni et al. "Alterations of the outer membrane composition in *Escherichia coli* lacking the histone-like protein Hu," *Proc. Nat. Acad. Sci. U.S.A.*, 94:6712-6717, 1997.

Sagt et al., "Impaired cutinase secretion in *Saccharomyces cerevisiae* induces irregular endoplasmic reticulum (ER) membran proliferation, oxidative stress, and ER-associated degradation," *Appl. Environ. Microbiol.*, 68(5):2155-2160, 2002.

Samuelson et al., "YidC mediates membrane protein insertion in bacteria," *Nature*, 406:637-641, 2000.

Schier et al., "Isolation of high-affinity monomeric human anti-c-erbB-2 single chain Fv using affinity-driven selection," *J. Mol. Biol.*, 255:28-43, 1996.

Seydel et al., "Testing the '2+ rule' for lipoprotein sorting in the *Escherichia coli* cell envelope with a new genetic selection," *Mol. Microbiol.*, 34(4):810-821, 1999.

Somerville et al., "Bacterial aspects assiciated with the expresion of a single-chain antibody fragment in *Escherichia coli*," *Appl. Microbiol. Biotechnol*, 42:595-603, 1994.

Stathopoulos et al., "Characterization of *Escherichia coli* expressing an Lpp'OmpA(46-159)-PhoA fusion protein localized in the outer membrane," *Appl. Microbiol. Biotechnol.*, 45:112-119, 1996.

Staudenmaier et al. "Nucleotide sequences of the fecbcde genes and locations of the proteins suggest a periplasmic-binding-protein-dependent transport mechanism for iron (III) dicitrate in *Escherichia coli*," *Journal of Bacteriology*, May 1989, p. 2626-2633.

Wittrup, "The single cell as a microplate well," *Nat. Biotechnol*, 18:1039-1040, 2000.

Yakushi et al., "A new ABC transporter mediating the detachment of lipid-modified proteins from membranes," *Nat. Cell. Biol.*, 2:212-218, 2000.

Yakushi et al., "Lethality of the covalent linkage between mislocalized major outer membrane lipoprotein and the poptidoglycan of *Escherichia coli*," *Journal of Bacteriology*, 179(9):2857, 1997.

Yamaguchi, "A single amino acid determinant of the membrane localization of lipoproteins in *E. coli*," *Cell*, 53(3):423-432, 1988.

Yu et al., "Lipoprotein-28, a cytoplasmic membrane lipoprotein from *Escherichia coli*," *J. Biol. Chem.*, 261(5):2284-2288, 1986.

Office Action issued in Canadian Application No. 2,645,194, mailed Nov. 17, 2010.

* cited by examiner

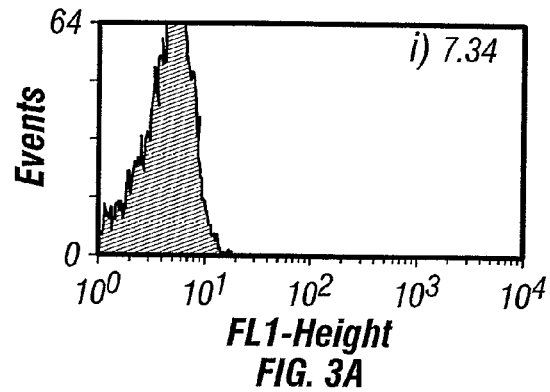
FIG. 3A
FIG. 3C
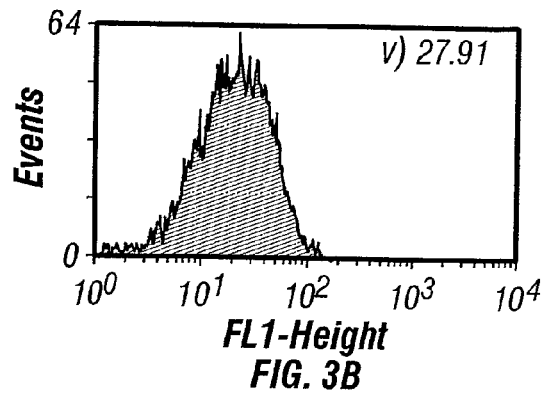
FIG. 3B
FIG. 3D
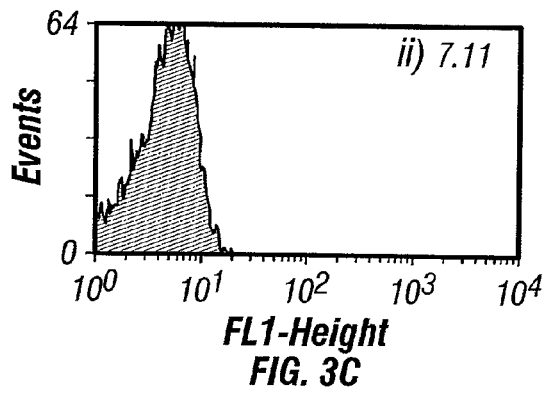
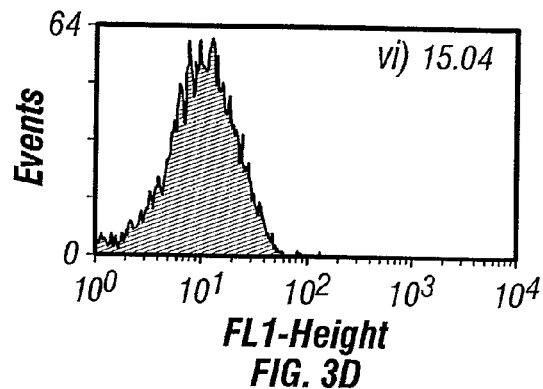
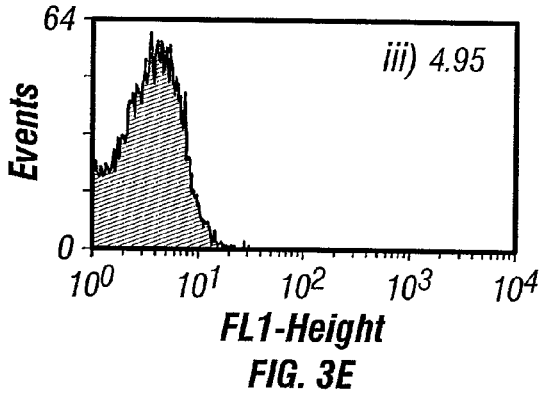
FIG. 3E
FIG. 3G
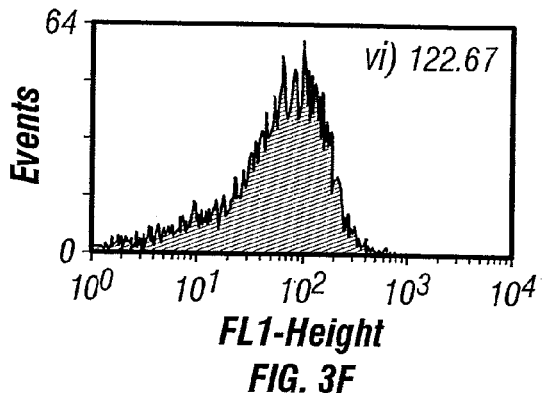
FIG. 3F
FIG. 3H
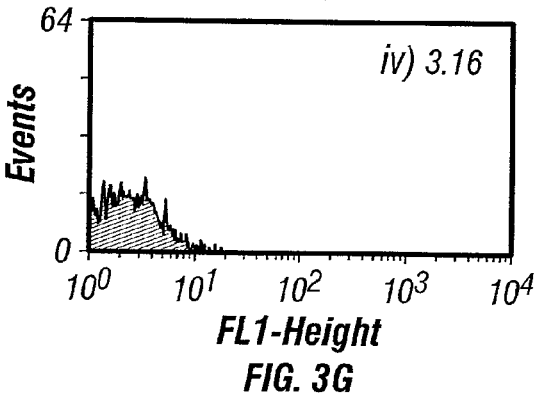
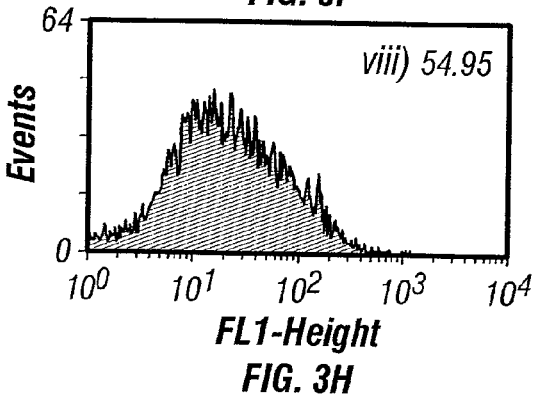

```
                              10
GlnValGlnLeuLeuGlnSerAlaAlaGluValLysLysProGlyGluSerLeuLys
CAGGTGCAGCTGTTGCAGTCTGCAGCAGAGGTGAAAAAGCCCGGGGAGTCTCTGAAG
      G AG      GG G  GCT GTC       T  A G   C     GA
      ValGlu   GlyGlyGlyLeuVal                Gly    Arg 20                          30       CDR1
IleSerCysLysGlySerGlyTyrSerPheThrSerTyrTrpIleGlyTrpValArg
ATCTCCTGTAAGGGTTCTGGATACAGCTTTACCAGCTACTGGATCGGCTGGGTGCGC
C        GCA CC      T  C     C GTGA       AC  GA    A C
Leu      AlaAla      PheThr    SerAsp       TyrMetSer Ile 40                                      52a
GlnMetProGlyLysGlyLeuGluTrpMetGlyIleIleTyrProGlyAspSerAsp
CAGATGCCCGGGAAAGGCCTGGAGTGGATGGGGATCATCTATCCTGGTGACTCTGAT
    GCT A     G  G       G TTCATAC  TAG AG A    GTAGTACC
    Ala                    ValSerTyr  SerSerSerGly   Thr

CDR2                           70
ThrArgTyrSerProSerPheGlnGlyGlnValThrIleSerAlaAspLysSerIle
ACCAGATACAGCCCGTCCTTCCAAGGCCAGGTCACCATCTCAGCCGACAAGTCCATC
  TATAC   GCAGAC  TG GA G    GAT       CAGG    CG    AG
  IleTyr  AlaAsp  ValLys     ArgPhe    Arg     AsnAlaLys 80        82a b c                          90
SerThrAlaTyrLeuGlnTrpSerSerLeuLysAlaSerAspThrAlaValTyrTyr
AGCACCGCCTACCTGCAGTGGAGCAGCCTGAAGGCCTCGGACACGGCCGTGTATTAC
      A T ACTG T     AAT A         GA    GA
      AsnSerLeu      MetAsn        Arg   Glu

CDR3                                110
CysAlaArgAlaSerProSerGlyPheAspTyrTrpGlyGlnGlyThrLeuValThr
TGTGCAAGAGCTTCTCCTTCGGGGTTTGACTATTGGGGCCAAGGTACCCTGGTCACC
         ACGGG TT C
         ThrGlyPhePro
              A G AT
              ThrTyr
ValSerSer
GTCTCGAGT             FIG. 7A
```

```
                                                                    20
CAGTCTGTGCTGACTCAGCCACCCTCAGCGTCTGGGACCCCCGGGCAGAGGGTCACC
GlnSerValLeuThrGlnProProSerAlaSerGlyThrProGlyGlnArgValThr

CDR1        31  a   b
ATCTCTTGTTCTGGAAGCAGCTCCAACATCGGAAGTAATTATGTATACTGGTACCAG
IleSerCysSerGlySerSerSerAsnIleGlySerAsnTyrValTyrTrpTyrGln

40                                          CDR2
CAGCTCCCAGGAACGGCCCCCAAACTCCTCATCTATAGGAATAATCAGCGGCCCTCA
GlnLeuProGlyThrAlaProLysLeuLeuIleTyrArgAsnAsnGlnArgProSer 60                          70
GGGGTCCCTGACCGATTCTCTGGCTCCAAGTCTGGCACCTCAGCCTCCCTGGCCATC
GlyValProAspArgPheSerGlySerLysSerGlyThrSerAlaSerLeuAlaIle

80                                              CDR3
AGTGGGCTCCGGTCCGAGGATGAGGCTGATTATTACTGTGCAGCATGGGATGACAGC
SerGlyLeuArgSerGluAspGluAlaAspTyrTyrCysAlaAlaTrpAspAspSer 95  a   b               100
CTGCGGGCTGTTGTATTCGGCGGAGGGACCAAGCTGACCGTCCTA
LeuArgAlaValValPheGlyGlyGlyThrLysLeuThrValLeu
  G    G  CC
  GlyGlyPro
  CTCG ---
  ProArg---
```

*FIG. 7B*

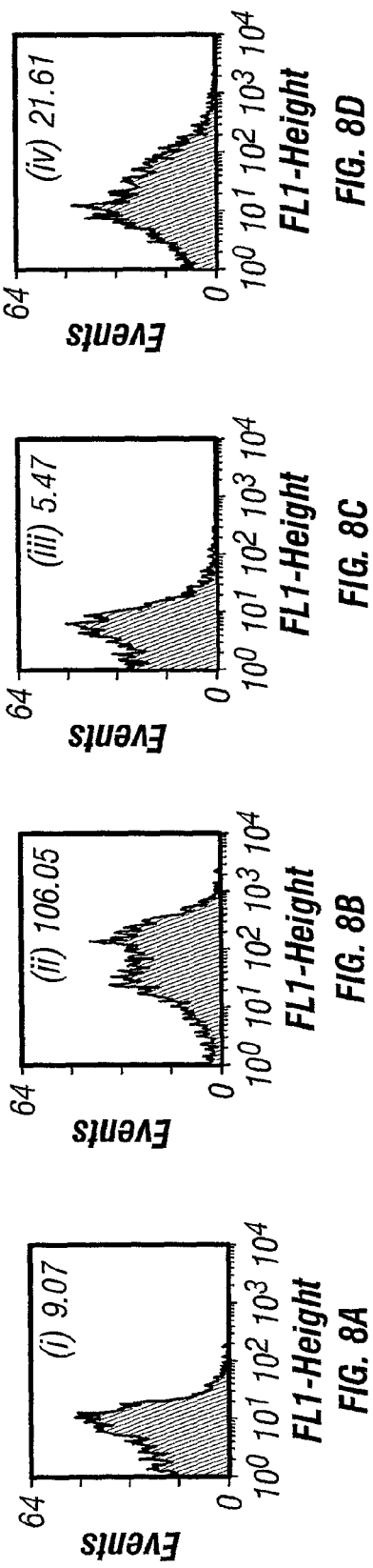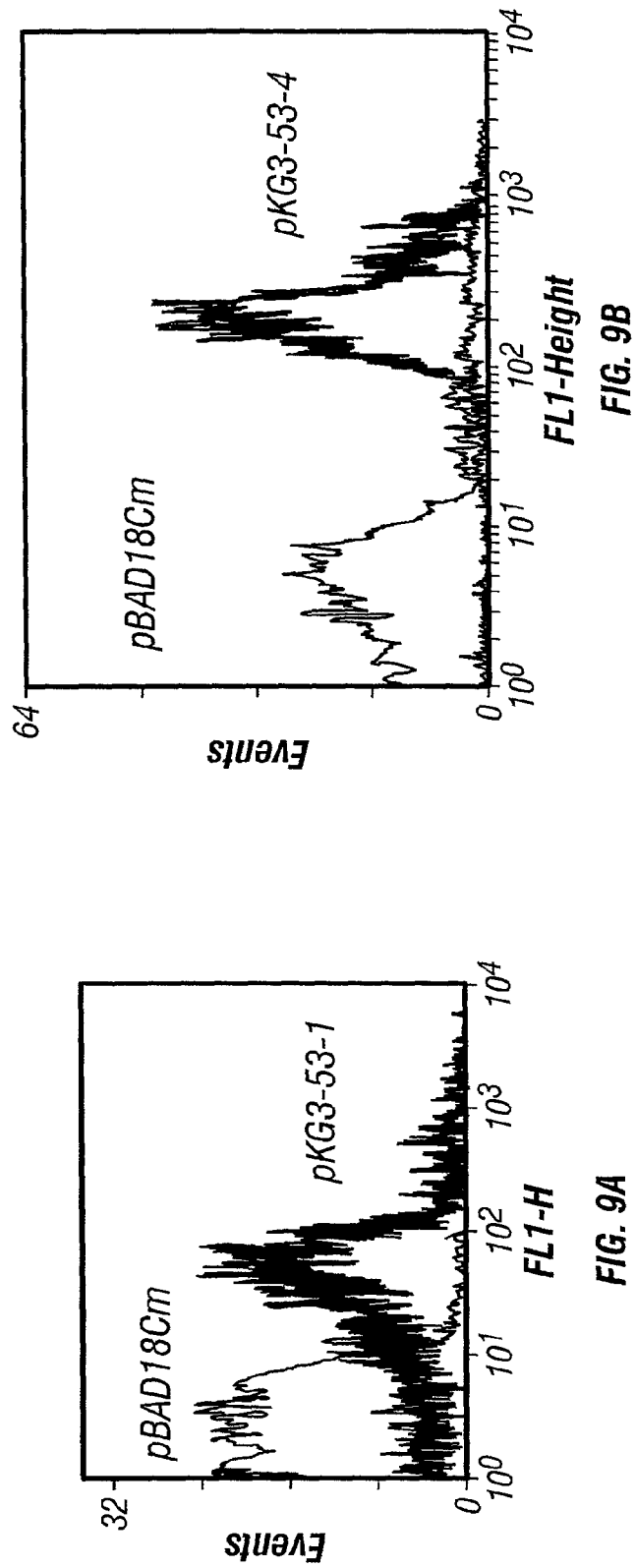

ISOLATION OF BINDING PROTEINS WITH HIGH AFFINITY TO LIGANDS

This application is a divisional application of currently application Ser. No. 09/699,023, filed Oct. 27, 2000 now U.S. Pat. No. 7,083,945, the contents of which are incorporated herein by reference.

The government owns rights in the invention pursuant to DARPA Grant No. MDA(972-97-0009).

BACKGROUND OF THE INVENTION

1. Field of the Invention

The present invention relates generally to the field of protein engineering. More particularly, it concerns methods for the screening of combinatorial libraries of polypeptides to allow isolation of enzymes having a desired catalytic activity and of ligand binding proteins, including antibodies and binding proteins having affinity for selected ligands

2. Description of Related Art

The isolation of proteins that either bind to ligands with high affinity and specificity or catalyze the enzymatic conversion of a reactant (substrate) into a desired product is a key process in biotechnology. Ligand-binding proteins and enzymes with a desired substrate specificity can be isolated from large libraries of mutants, provided that a suitable screening method is available. Small protein libraries composed of $10^3$-$10^5$ distinct mutants can be screened by first growing each clone separately and then using a conventional assay for detecting clones that exhibit specific binding. For example, individual clones expressing different protein mutants can be grown in microtiter well plates or separate colonies on semisolid media such as agar plates. To detect binding the cells are lysed to release the proteins and the lysates are transferred to nylon filters, which are then probed using radiolabeled or fluorescently labeled ligands (DeWildt et al. 2000). However, even with robotic automation and digital image systems for detecting binding in high density arrays, it is not feasible to screen large libraries consisting of tens of millions or billions of clones. The screening of libraries of that size is required for the de novo isolation of enzymes or protein binders that have affinities in the nanomolar range.

The screening of very large protein libraries has been accomplished by a variety of techniques that rely on the display of proteins on the surface of viruses or cells (Ladner et al. 1993). The underlying premise of display technologies is that proteins engineered to be anchored on the external surface of biological particles (i.e., cells or viruses) are directly accessible for binding to ligands without the need for lysing the cells. Viruses or cells displaying proteins with affinity for a ligand can be isolated in a variety of ways including sequential adsorption/desorption form immobilized ligand, by magnetic separations or by flow cytometry (Ladner et al. 1993, U.S. Pat. No. 5,223,409, Ladner et al. 1998, U.S. Pat. No. 5,837,500, Georgiou et al. 1997, Shusta et al. 1999). The most widely used display technology for protein library screening applications is phage display. Phage display is a well-established and powerful technique for the discovery of proteins that bind to specific ligands and for the engineering of binding affinity and specificity (Rodi and Makowski, 1999). In phage display, a gene of interest is fused in-frame to phage genes encoding surface-exposed proteins, most commonly pIII. The gene fusions are translated into chimeric proteins in which the two domains fold independently. Phage displaying a protein with binding affinity for a ligand can be readily enriched by selective adsorption onto immobilized ligand, a process known as "panning". The bound phage is desorbed from the surface, usually by acid elution, and amplified through infection of $E.\ coli$ cells. Usually, 4-6 rounds of panning and amplification are sufficient to select for phage displaying specific polypeptides, even from very large libraries with diversities up to $10^{10}$ Several variations of phage display for the rapid enrichment of clones displaying tightly binding polypeptides have been developed (Duenas and Borrebaeck, 1994; Malmborg et al., 1996; Kjaer et al., 1998; Burioni et al., 1998; Levitan, 1998; Mutuberria et al., 1999; Johns et al., 2000).

One of the most significant applications of phage display technology has been the isolation of high affinity antibodies (Dall'Acqua and Carter, 1998; Hudson et al., 1998; Hoogenboom et al., 1998; Maynard and Georgiou, 2000). Very large and structurally diverse libraries of scFv or $F_{AB}$ fragments have been constructed and have been used successfully for the in vitro isolation of antibodies to a multitude of both synthetic and natural antigens (Griffiths et al., 1994; Vaughan et al., 1996; Sheets et al., 1998; Pini et al., 1998; de Haard et al., 1999; Knappik et al., 2000; Sblattero and Bradbury, 2000). Antibody fragments with improved affinity or specificity can be isolated from libraries in which a chosen antibody had been subjected to mutagenesis of either the CDRs or of the entire gene CDRs (Hawkins et al., 1992; Low et al., 1996; Thompson et al., 1996; Chowdhury and Pastan, 1999). Finally, the expression characteristics of scFv, notorious for their poor solubility, have also been improved by phage display of mutant libraries (Deng et al., 1994; Coiaetal., 1997).

However, several spectacular successes notwithstanding, the screening of phage-displayed libraries can be complicated by a number of factors. First, phage display imposes minimal selection for proper expression in bacteria by virtue of the low expression levels of antibody fragment gene III fusion necessary to allow phage assembly and yet sustain cell growth (Krebber et al., 1996, 1997). As a result, the clones isolated after several rounds of panning are frequently difficult to produce on a preparative scale in $E.\ coli$. Second, although phage displayed proteins may bind a ligand, in some cases their un-fused soluble counterparts may not (Griep et al., 1999). Third, the isolation of ligand-binding proteins and more specifically antibodies having high binding affinities can be complicated by avidity effects by virtue of the need for gene III protein to be present at around 5 copies per virion to complete phage assembly. Even with systems that result in predominantly monovalent protein display, there is nearly always a small fraction of clones that contain multiple copies of the protein. Such clones bind to the immobilized surface more tightly and are enriched relative to monovalent phage with higher affinities (Deng et al., 1995; MacKenzie et al., 1996, 1998). Fourth, theoretical analysis aside (Levitan, 1998), panning is still a "black box" process in that the effects of experimental conditions, for example the stringency of washing steps to remove weakly or non-specifically bound phage, can only be determined by trial and error based on the final outcome of the experiment. Finally, even though pIII and to a lesser extent the other proteins of the phage coat are generally tolerant to the fusion of heterologous polypeptides, the need to be incorporated into the phage biogenesis process imposes biological constraints that can limit library diversity. Therefore, there is a great need in the art for techniques capable of overcoming these limitations.

Protein libraries have also been displayed on the surface of bacteria, fungi, or higher cells. Cell displayed libraries are typically screened by flow cytometry (Georgiou et al. 1997, Daugherty et al. 2000). However, just as in phage display, the protein has to be engineered for expression on the cell surface. This imposes several potential limitations. First of all, either the N-terminal or the C-terminal of the protein has to be fused to a vehicle for display. Thus, these technologies are not suitable where the N- or C-termini are essential for ligand binding. Second, the requirement for display of the protein on the surface of a cell imposes biological constraints that limit the diversity of the proteins and protein mutants that can be screened. Third, complex proteins consisting of several polypeptide chains cannot be readily displayed on the surface of bacteria, filamentous phages or yeast. As such, there is a great need in the art for technology which circumvents all the above limitations and provides an entirety novel means for the screening of very large polypeptide libraries.

At present, the isolation of novel enzymes from libraries of protein mutants is typically accomplished either through the use of a phenotypic selection or screening in either solid phase or microtiter well plates. Biological selections are based on complementation of auxotrophy or resistance to cytotoxic agents (e.g., antibiotics). Unfortunately, the utility of phenotypic selections is limited to the isolation of catalysts for reactions that are of direct biological relevance or can be indirectly linked to a selectable phenotype. Alternatively, each clone in a mutant population may be screened directly for enzymatic activity. For libraries expressed in microorganisms, screening can be performed on colonies growing on a solid substrate such as agar. Solid phase screening relies on substrates of an enzymatic reaction that give rise to a zone of clearance, a fluorescent product, or a strongly absorbing (chromogenic) product. The assay may detect the enzyme product directly or may be coupled to a second enzyme whose product can in turn be easily monitored. However, many assays cannot be implemented in a solid phase format. If that is the case then individual clones must be grown and assayed in microtiter wells. Such assays are significantly more time consuming than solid phase assays and severely limit the number of mutants that can be screened. However, when a small number of random mutants is screened, the probability of finding clones expressing an enzyme that can catalyze a desired biotransformation, especially when that biotransformation requires a complicated reaction, is severely affected.

In general, methods that will allow the screening of large libraries of enzyme mutants on the basis of kinetic parameters, i.e., on the basis of how much product is generated per unit time, are needed. Phage display technology may in principle be used as a tool for the isolation of useful enzymes from large libraries. However, harnessing phage display technology for the isolation of enzyme catalysts from libraries has thus far not proven practical (Olsen et al. 2000). For example there is no apparent way to physically link in a quantitative manner a phage particle displaying a certain enzyme clone with the outcome of multiple catalytic turnovers resulting in the accumulation of reaction product. Establishing such a linkage is essential for the screening of protein libraries on the basis of catalytic proficiency.

SUMMARY OF THE INVENTION

In one aspect, the invention provides a method of obtaining a bacterium comprising a nucleic acid sequence encoding a binding protein capable of binding a target ligand, the method comprising the steps of: (a) providing a Gram negative bacterium comprising a nucleic acid sequence encoding a candidate binding protein, wherein the binding protein is expressed in soluble form in the bacterium; (b) contacting the bacterium with a labeled ligand capable of diffusing into the bacterium; and (c) selecting the bacterium based on the presence of the labeled ligand within the bacterium, wherein the ligand and the candidate binding protein are bound in the bacterium.

In another aspect, the invention provides a method of obtaining a nucleic acid sequence encoding a binding protein capable of binding a target ligand, the method comprising the step of: (a) providing a Gram negative bacterium comprising a nucleic acid sequence encoding a candidate binding protein, wherein the binding protein is expressed in soluble form in the bacterium; (b) contacting the bacterium with a labeled ligand capable of diffusing into the bacterium; (c) selecting the bacterium based on the presence of the labeled ligand within the bacterium, wherein the ligand and the candidate binding protein are bound in the bacterium; and (d) cloning the nucleic acid sequence encoding the candidate binding protein.

In another aspect of the invention, the binding protein expressed in the bacterium is further defined as expressed in soluble form in the periplasm of the bacterium. The nucleic acid sequence encoding the binding protein may still further be defined as encoding a nucleic acid sequence comprising the candidate binding protein sequence operably linked to a leader sequence capable of directing expression of the candidate binding protein in the periplasm. Potentially any Gram negative bacterium could be used with the invention, including, for example, an *E. coli* bacterium. In one embodiment of the invention, the nucleic acid sequence encoding a candidate binding protein may be further defined as capable of being amplified following the selection. The invention may still further be defined as including removing labeled ligand not bound to the candidate binding protein.

In yet another aspect, the invention comprises providing a population of Gram negative bacteria. In one embodiment of the invention, the population of bacteria is further defined as collectively capable of expressing a plurality of candidate binding proteins. In yet another embodiment of the invention, the population of bacteria is obtained by a method comprising the steps of: a) preparing a plurality DNA inserts which collectively encode a plurality of different potential binding proteins, and b) transforming a population of gram negative bacteria with the DNA inserts. The population of Gram negative bacteria may be still further defined as contacted with the labeled ligand.

In still yet another aspect of the invention, a candidate binding protein employed in accordance with the invention is further defined as an antibody or fragment thereof, or alternatively, is a binding protein other than an antibody. Still further, the candidate binding protein may be an enzyme, including any portion thereof. A candidate binding protein used with the invention may be further defined as not capable of diffusing out of the periplasm in intact bacteria.

In still yet another aspect of the invention, a labeled ligand may comprise a polypeptide, an enzyme and/or a nucleic acid or the like. The labeled ligand may be further defined as comprising a molecular weight of less than about 20,000 Da, less than about 10,000 Da or less than about 5,000 Da, and may in other embodiments of the invention be described as greater than 600 Da in molecular weight. The labeled ligand may be still further defined as fluorescently labeled.

In still yet another aspect, the invention comprises treating a bacterium to facilitate diffusing of a target ligand into the periplasm. In certain embodiments of the invention, the treating may comprise use of hyperosmotic conditions, physical stress, treating the bacterium with a phage, or growing the bacterium at a sub-physiological temperature, for example, about 25° C.

In still yet another aspect, the invention comprises selecting one or more bacteria using FACS or magnetic separation. In the invention, the ligand and candidate binding protein may be further defined as reversibly bound in the periplasm.

In still yet another aspect, the invention provides a method of obtaining a bacterium comprising a nucleic acid sequence encoding a catalytic protein catalyzing a chemical reaction involving a target substrate, the method comprising the steps of: (a) providing a Gram negative bacterium comprising a nucleic acid sequence encoding a candidate catalytic protein, wherein the catalytic protein is expressed in soluble form in the bacterium; (b) contacting the bacterium with a target substrate capable of diffusing into the bacterium, wherein the candidate catalytic protein catalyzes a chemical reaction involving the target substrate and wherein the chemical reaction yields at least a first substrate product; and (c) selecting the bacterium based on the presence of the first substrate product. In yet another aspect of the invention, the method may be further defined as a method of obtaining a nucleic acid sequence encoding a catalytic protein catalyzing a reaction with a target substrate, the method further comprising the step of: (d) cloning the nucleic acid sequence encoding the candidate catalytic protein. By "catalytic protein" it is meant a molecule which is capable of increasing the rate of a chemical reaction relative to the rate the reaction would occur absent the catalytic protein. In the method, the candidate catalytic protein may be expressed in soluble form in the periplasm of the bacterium. The nucleic acid sequence encoding a candidate catalytic protein may, in further embodiments of the invention, be defined as operably linked to a leader sequence capable of directing expression of the candidate catalytic protein in the periplasm.

In still yet another aspect, the aforementioned method may be carried out with any Gram negative bacterium, for example, an *E. coli* bacterium. The invention may also comprise providing a population of Gram negative bacteria. The population may be further defined as collectively capable of expressing a plurality of candidate catalytic proteins. In one embodiment of the invention, the population of bacteria is obtained by a method comprising the steps of: a) preparing a plurality DNA inserts which collectively encode a plurality of different candidate catalytic proteins, and b) transforming a population of Gram negative bacteria with the DNA inserts. The Gram negative bacteria may be defined as contacted with the target substrate. A bacterium selected with the invention may be further defined as viable following the selecting. Selecting may be carried out by any desired method, for example, FACS or magnetic separation.

In still yet another aspect of the invention, a candidate catalytic protein is an enzyme. The candidate catalytic protein may also be defined as not capable of diffusing out of the periplasm.

In still yet another aspect of the invention, a target substrate may comprise a molecule containing a scissile amide bond. The target substrate may also comprise a polypeptide or a nucleic acid. In certain embodiments of the invention, the target substrate comprises a molecule containing a scissile carboxylic ester bond, a molecule containing a scissile phosphate ester bond, a molecule containing a scissile sulfonate ester bond, a molecule containing a scissile carbonate ester bond, a molecule containing a scissile carbamate bond, and/ or a molecule containing a scissile thioester bond. In still further embodiments of the invention, the target substrate is further defined as comprising a molecular weight of less than about 20,000 Da, less than about 5,000 Da, less than about 3,000 Da, or may be defined as comprising a molecular weight of greater than about 600 Da, including from about 600 Da to about 30,000 Da.

In still yet another aspect of the invention, the first substrate product is further defined as capable of being detected based on the presence of a fluorescent signature. This fluorescent signature may be absent in the target substrate, and may only be produced upon chemical reaction to produce the first substrate product. In one embodiment of the invention, a fluorescent signature is produced by catalytic cleavage of a scissile bond. The method may be further defined as comprising use of a FRET system, the FRET system comprising a fluorophore bound by a scissile bond to at least a first molecule capable of quenching the fluorescence of the fluorophore, wherein cleavage of the scissile bond allows the first molecule to diffuse away from the fluorophore and wherein the fluorescence of the fluorophore becomes detectable. In the method, the fluorophore may comprise a positive charge allowing the fluorophore to remain associated with the bacterium. In further embodiments of the invention, the target substrate may be further defined as comprising a latent fluorescent moiety capable of being released by the chemical reaction involving the target substrate. The latent fluorescent moiety released by the cleavage may possess an overall positive charge allowing the moiety to remain associated with the bacterium following the cleavage. In yet another embodiment of the invention, the method may comprise labeling the target substrate with a fluorescent pH probe capable of being detected upon a change in pH associated with the chemical reaction involving the target substrate. The fluorescent pH probe may possess an overall positive charge allowing the fluorescent pH probe to remain associated with the bacterium following the chemical reaction involving the target substrate. It will be understood by those of skill in the art that multiple products may be produced as a result of the chemical reaction and any one or more of these could potentially be detected to reveal that occurrence of the chemical reaction. Accordingly, the reaction product may comprise a change in pH within the bacterium which could be detected.

In still yet another aspect, the invention may comprise treating the bacterium to facilitate the diffusing into the periplasm, for example, using hyperosmotic conditions, physical stress, treating the bacterium with a phage, and growing the bacterium at a sub-physiological temperature, for example, about 25° C.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A, FIG. 4C, FIG. 4E, FIG. 4G: pHEN2.thy; FIG. 4B, FIG. 4D, FIG. 4F, FIG. 4H pHEN2.dig; FIG. 4A and FIG. 4B, 1×PBS; FIG. 4C and FIG. 4D, 2.5×PBS; FIG. 4E and FIG. 4F 5×PBS; FIG. 4G and FIG. 4H 10×PBS.

FIG. 5A pHEN.thy; FIG. 5C pHEN2.thy/M13K07; pHEN2.dig; FIG. 5D pHEN2.dig/M13K07.

FIG. 6A: Phage eluate titers, after each round of panning FIG. 6B: Polyclonal phage ELISA of purified phage stocks on digoxin-ovalbumin. FIG. 6C: FACScanning naïve library FIG. 6C-1 and rounds one to five (FIG. 6C-2 to FIG. 6C-6) of panning on digoxin-BSA using BODIPY™-digoxygenin.

FIG. 7A, B. Amino acid and nucleotide sequences of scFv antibody fragments isolated by expression in the periplasm and FACS. FIG. 7A: Heavy chain of dig1 is shown in true font while dig3 is shown in italics underneath. The nucleotide sequences corresponding to the heavy chains of dig 1 and dig 3 are given by SEQ ID NO:17 and SEQ ID NO:18, respectively. Dig2 variation from dig 1 is as indicated in underlined text within CDR3. FIG. 7B: Light chain of dig1, 2 and 3 with variations in CDR3 indicated as for heavy chain. The nucleotide sequences corresponding to the light chains of dig1 and dig 3 are given by SEQ ID NO:19 and SEQ ID NO:20, respectively. The underlined four nucleotide variation beginning at nucleotide 99 is given by SEQ ID NO:21.

FIGS. 8A-8D. Labeling of periplasmic scFv by fluorescently tagged oligonucleotide probe. ABLE™C cells expressing periplasmic scFv specific for either atrazine as a negative control (FIG. 8A and FIG. 8C) or for digoxin (FIG. 8B and FIG. 8D) were labeled either with: 100 nM with digoxigenin-BODIPY™(FIG. 8A and FIG. 8B) or 100nM of dig-5A-FL (FIG. 8C and FIG. 8D). 10,000 events were recorded using a FACSort flow cytometer at a rate of approximately 1,000 events per second.

FIGS. 9A-9B. Fluorescence discrimination of E. coli expressing the enzyme cutinase (an esterase) from control bacteria not expressing the enzyme. E. coli DH5acells were transformed either with the plasmid pBAD18Cm (control cells) or with the derivative plasmid pKG3-53-1 encoding the Fusarium solani enzyme cutinase. FIG. 9A. Fluorescence histogram showing the selective labeling of E. coli expressing cutinase in the periplasm (pkg3-53-1 containing-cells) using a fluorescent esterase substrate (10μM Fluorescein Dibutyrate) for 30 minutes at 37° C. FIG. 9B. Fluorescence histogram of from selective labeling of cutinase-expressing cells (transcribed from the pKG3-53-4 vector) labeled with a fluorescent pH-Sensitive Dye (1μM LysoSensor Green DND-189) in the presence of cutinase substrate (1 mM 4-Nitrophenyl Butyrate). The cells were labeled for 5 minutes at 25° C. Acidification of the periplasm occurred as a result of ester hydrolysis by the cutinase.

DESCRIPTION OF ILLUSTRATIVE EMBODIMENTS

The present technology circumvents the limitations of the prior art and provides an entirety novel means for the screening of very large polypeptide libraries. In particular, the invention overcomes deficiencies in the prior art by providing a rapid approach for isolating proteins that bind to small molecules and peptides via "display-less" library screening. A description of an example of such a process in accordance with the invention is described for illustrative purposes in FIG. 1. In the technique, libraries of candidate binding proteins, such as antibody sequences, are expressed in soluble form in the periplasmic space of gram negative bacteria, such as *Escherichia coli*, and are mixed with a labeled ligand. The periplasm comprises the space defined by the inner and outer membranes of a gram-negative bacterium.

Figure 1:
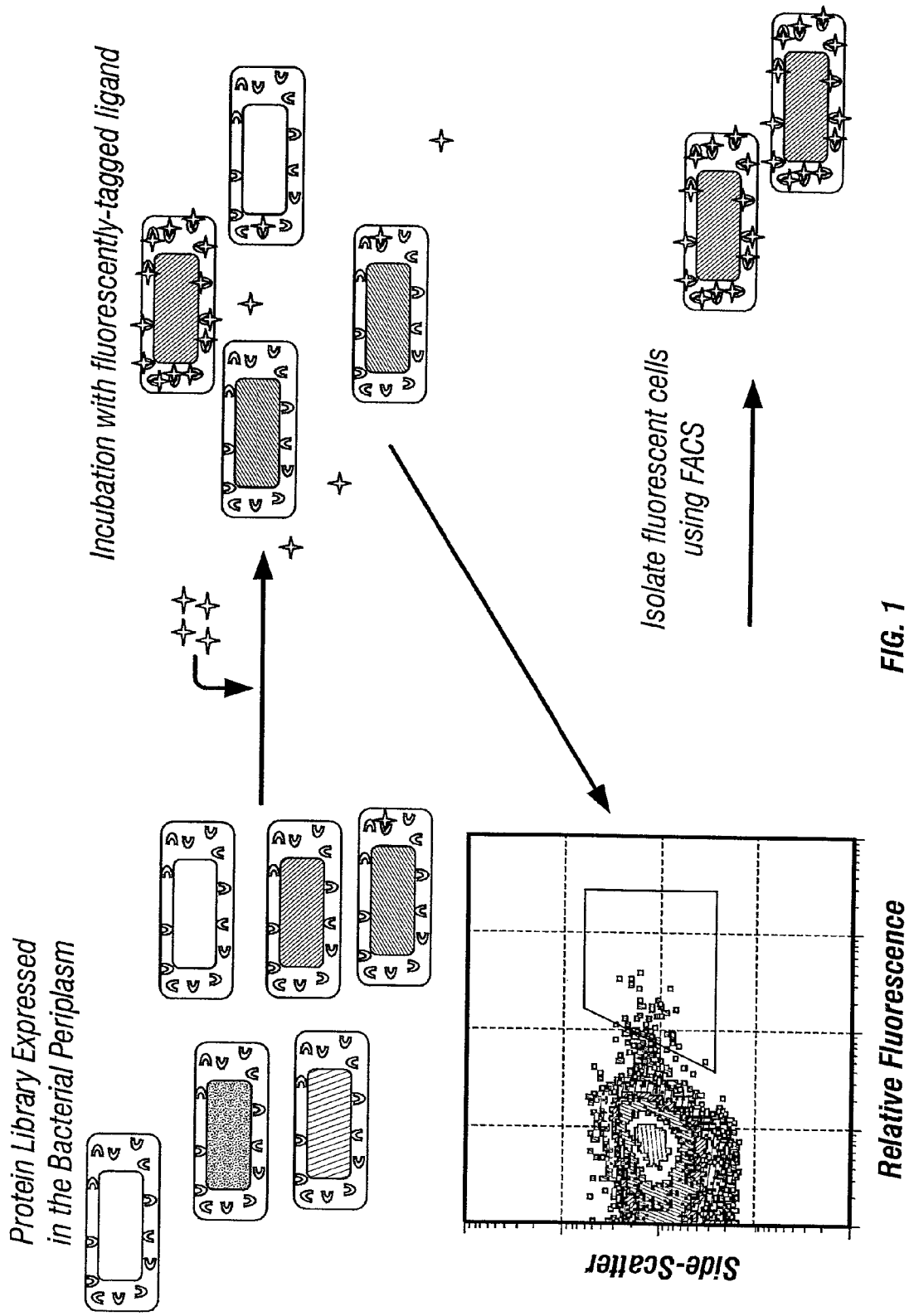
FIG. 1. General scheme of the basis of a preferred embodiment of the invention. A library of proteins expressed in the periplasmic space of bacteria is contacted with a fluorescent reagent. Bacterial clones expressing a protein having a desired activity (e.g., either binding of the probe or enzymatic conversion to a product) become fluorescently labeled. The fluorescent cells can subsequently be isolated by FACS.
Figure 2A:
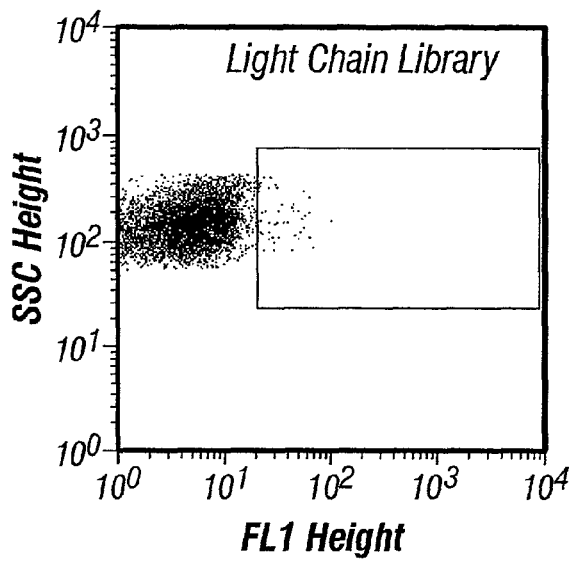
FIG. 2. Isolation of affinity improved mutants of an anti-digoxin antibody by two rounds of sorting. A library of scFv mutants in which three residues in the light chain had been randomized was constructed as described in Example 2. A total of $2.5 \times 10^6$ transformants were grown in liquid media, labeled with 100 nM digoxin-BODIPY™ and fluorescent cells falling within the window shown in the rightmost panel were sorted by FACS. The sorted cells were grown in liquid media, re-labeled and cells falling within the specified window as shown in the center panel were isolated. Following a final round of re-growth the cells were analyzed by FACS (left-most panel). Single scFv antibody colonies were picked at random, analyzed and the affinity of the corresponding scFv proteins are reported in Table 1.
Figure 2B:
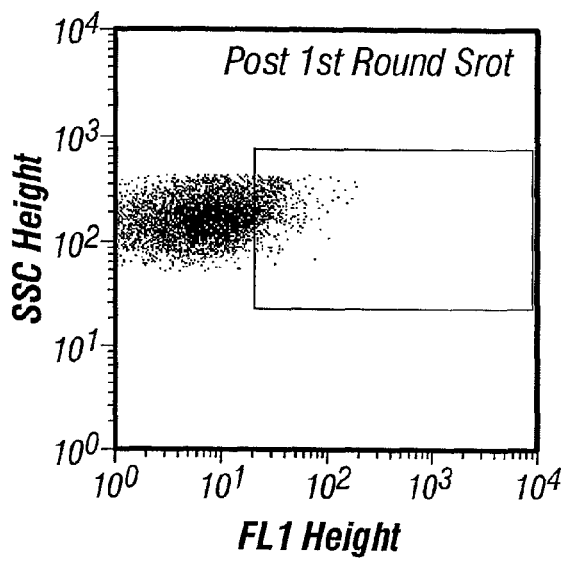
Figure 2C:
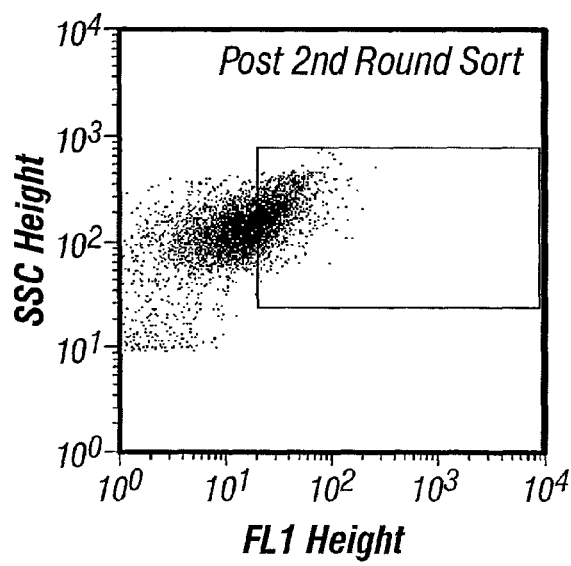
Figure 4A:
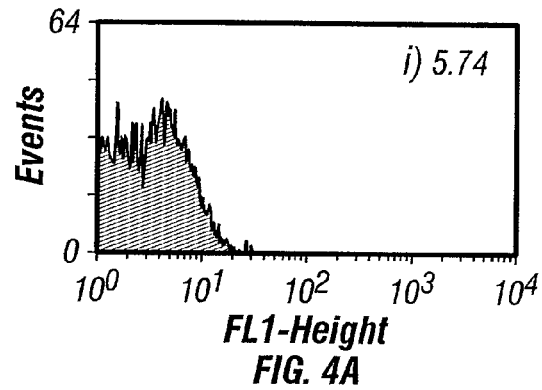
FIGS. 4A-4H. Effect of hyperosmotic shock on labeling efficiency.
Figure 4B:
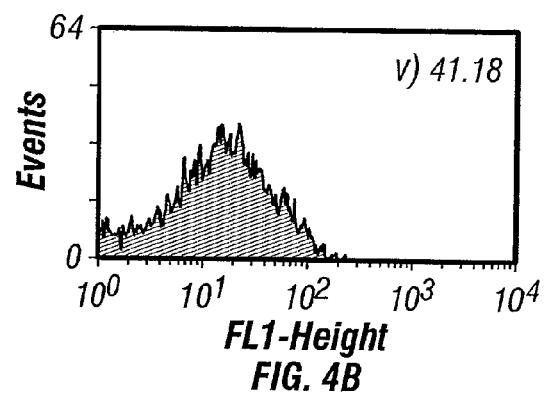
Figure 4C:
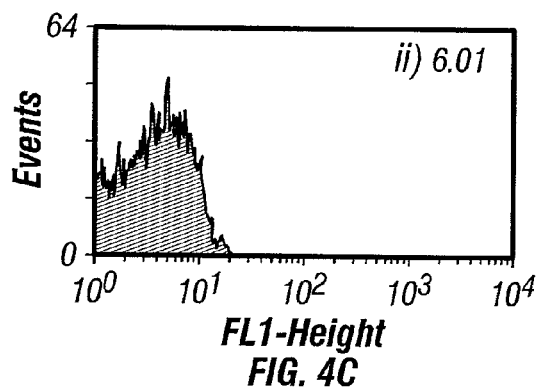
Figure 4D:
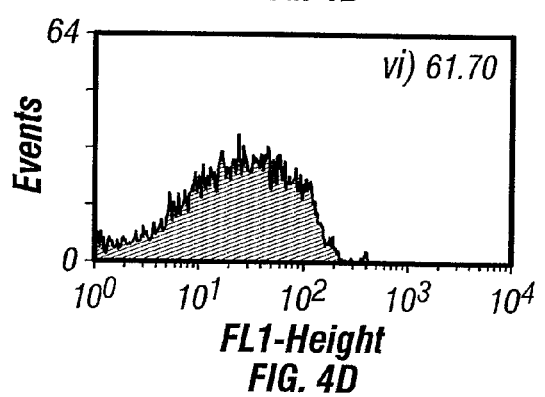
Figure 4E:
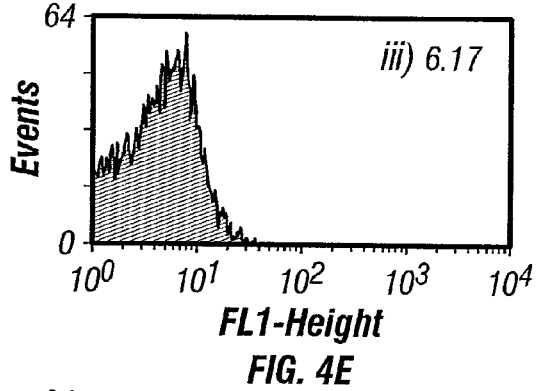
Figure 4F:
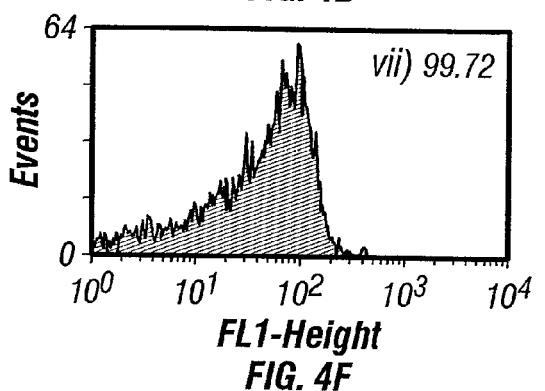
Figure 4G:
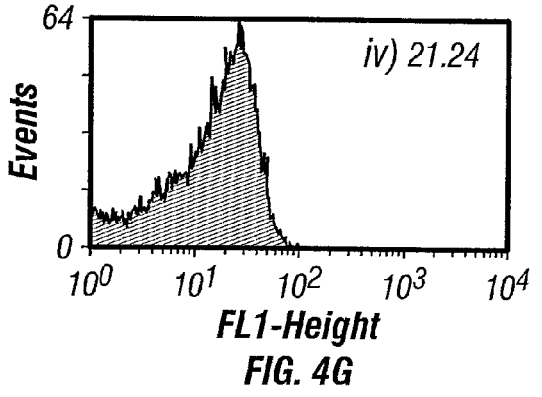
Figure 4H:
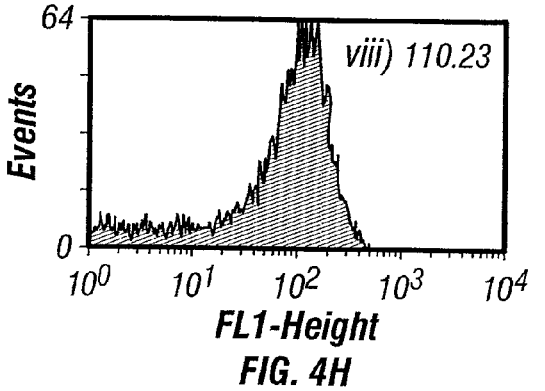
Figure 5A:
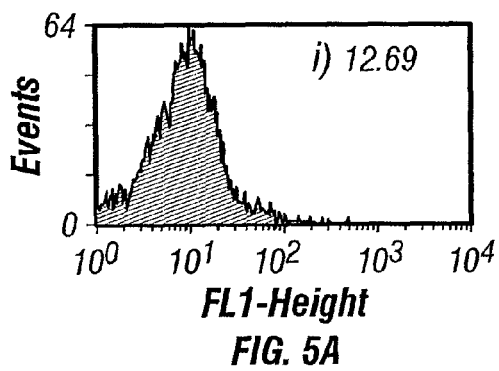
FIGS. 5A-5D. Maximizing periplasmic FACS signal in ABLE™C labeled in 5×PBS using $P_{tac}$ vector and superinfection with M13KO7 (moi of 10) 0.5h pre-induction.
Figure 5B:
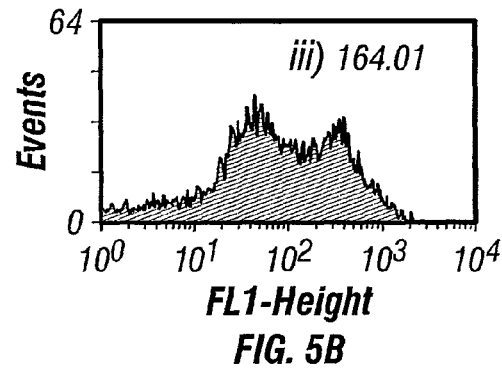
Figure 5C:
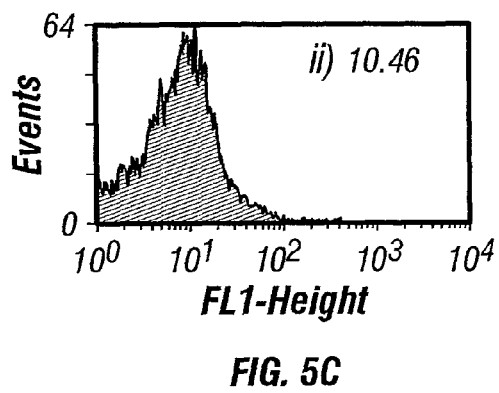
Figure 5D:
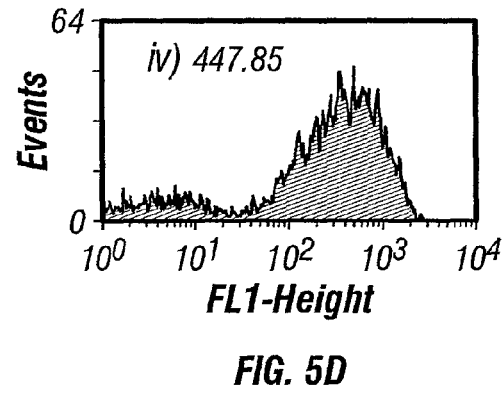

In wild-type *E. coli* and other gram negative bacteria, the outer membrane serves as a permeability barrier that severely restricts the diffusion of molecules greater than 600 Da into the periplasmic space (Decad and Nikado, 1976). Conditions that increase the permeability of the outer membrane, allowing larger molecules to diffuse in the periplasm, have two deleterious effects in terms of the ability to screen libraries: (a) the cell viability is affected to a significant degree and (b) the diffusion of molecules into the cell is accompanied by the diffusion of proteins and other macromolecules. The expressed proteins leak out of the periplasm and thus the resulting cell based libraries cannot be screened in a meaningful way. However, the inventors have identified experimental conditions such that allow fluorescent conjugates of ligands and polypeptides equilibrate across the outer membrane while proteins secreted into the periplasm remain within the cell. Therefore, in bacterial cells expressing recombinant polypeptides with affinity for the ligand, the concentration of the labeled ligand bound to the binding protein is increased, allowing the bacteria to be isolated from the rest of the library. Where fluorescent labeling of the target ligand is used, cells may efficiently be isolated by fluorescence activated cell sorting (FACS). Thus, in effect, the cell envelope serves as a "dialysis bag" that retains macromolecule:ligand complexes, but not free ligand (FIG. 1). With this approach, existing libraries of secreted proteins in bacteria can be easily tested for ligand binding without the need for subcloning into a phage or cell surface display system.

I. Anchor-Less Display Library Screening

Prior art methods of both phage display and bacterial cell surface display suffer from a limitation in that the protein is required, by definition, to be physically displayed on the surface of the vehicle used, to allow unlimited access to the targets (immobilized for phage or fluorescently conjugated ligands for FACS) (U.S. Pat. No. 5,223,409, the disclosure of which is specifically incorporated herein by reference in its entirety). Certain proteins are known to be poorly displayed on phage (Maenaka et al., 1996; Corey et al., 1993) and the toxic effects of cell surface display have been treated at length (Daugherty et al., 1999). The proteins to be displayed also need to be expressed as fusion proteins, which may alter their function. The selection constraints imposed by any display system may, therefore, limit the application to relatively small and "simple" proteins and deny access to a multitude of large and complex multisubunit species. The latter are very likely to be incapable of partaking efficiently in the complex process of phage assembly termination or outer-membrane translocation without very serious effects on host cell viability.

Herein, the inventors have described conditions whereby expressed binding proteins, for example, an antibody, are targeted to the periplasmic compartment of *E. coli* and yet are amenable to binding ligands and peptides of up to at least 2 kDa. As used herein, the term "binding protein" includes not only antibodies, but also fragments of antibodies, as well as any other polypeptide or protein potentially capable of binding a given target molecule. The antibody or other binding proteins may be expressed with the invention directly and not as fusion proteins. Such a technique may be termed "anchor-less-display" (ALD). To understand how it may work, one needs to be aware of the location in which it functions.

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteroploymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations ($Mg^{2+}$ and $Ca^{2+}$) and link each other electrostatically to form a highly ordered quasi-crystalline ordered "tiled roof" on the surface (Labischinski et al., 1985). The membrane forms a very strict permeability barrier of allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Naeke, 1976; Nikaido and Nakae, 1979; Nikaido and Vaara, 1985). With such strict physiological regulation of access by molecules to the periplasm it may appear, at first glance, inconceivable that ALD should work unless the ligands employed are at or below the 650 Da exclusion limit or are analogues of normally permeant compounds. However, the inventors have shown that ligands at least 2000 Da in size can diffuse into the periplasm. Such diffusion can be aided by one or more treatments of a bacterial cell, thereby rendering the outer membrane more permeable, as is described herein below.

II. Ligand Access to the Bacterial Periplasm

Certain classes of hydrophobic antibiotics, larger than the 650 Da exclusion limit, can diffuse through the bacterial outer membrane itself, independent of membrane porins (Farmer et al., 1999). The process may actually permeabilize the membrane on so doing (Jouenne and Junter, 1990). Such a mechanism has been adopted to selectively label the periplasmic loops of a cytoplasmic membrane protein in vivo with a polymyxin B nonapeptide (Wada et al., 1999). Also, certain long chain phosphate polymers (100 Pi) appear to bypass the normal molecular sieving activity of the outer membrane altogether (Rao and Torriani, 1988). However, such conditions generally lead to a decrease in cell viability. Maintaining the cells in a viable state is essential for library screening applications since non-viable cells cannot be propagated.

The inventors have defined conditions that lead to the permeation of ligands into the periplasm without loss of viability or release of the expressed proteins from the cells. As a result, cells expressing binding protein can be fluorescently labeled simply by incubating with a solution of fluorescently labeled ligand. The inventors have observed marked differences in labeling efficiencies of different strains of bacterial host cells. It has been shown previously that increased permeability due to OmpF overexpression was caused by the absence of a histone like protein resulting in a decrease in the amount of a negative regulatory MRNA for OmpF translation (Painbeni et al., 1997). Also, DNA replication and chromosomal segregation is known to rely on intimate contact of the replisome with the inner membrane, which itself contacts the outer membrane at numerous points. That the FACS optimal ABLEC strain has mutations altering plasmid copy number is thus, noteworthy.

The inventors also noticed that treatments such as hyperosmotic shock can improve labeling significantly. It is known that many agents including, calcium ions (Bukau et al., 1985) and even Tris buffer (Irvin et al., 1981) alter the permeability of the outer-membrane. Further, the inventors found that phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention comprising a judicious combination of strain, salt and phage, the inventors surpassed the highest fluorescent signal reported even for cell surface display of the antidigoxin antibody scFv (Daugherty et al., 1999). This result demonstrated that the anchor-less display methodology allows for excellent ligand-dependent labeling of cells. Cells labeled with a fluorescent ligand can then be easily isolated from cells that express non-binding protein mutants using flow cytometry or other related techniques.

III. Periplasmic Peptide Expression

In one embodiment of the invention, bacterial cells are provided expressing candidate molecules in the periplasm of the bacteria. An advantage of the instant invention is that, unlike prior art phage display techniques, it is not necessary that the candidate molecule be surface-bound, thereby limiting the potential for effects due to surface interactions with the candidate molecule, or limitations in the expression thereof. Thus, the invention employs "anchor-less display." The general scheme behind the technique of the invention is the advantageous expression of a heterogeneous collection of peptides in soluble form in the periplasm.

Methods that may be employed with the current invention for the expression of heterologous proteins in the periplasm of Gram negative bacteria are well known in the art (see, for example, U.S. Pat. Nos. 5,646,015 and 5,759,810, the disclosures of which are incorporated herein by reference in their entirety). In such techniques, bacterial-encoded heterologous proteins can be directed across the inner membrane of the bacterial cell envelope, into the space between the inner and the outer membrane known as the periplasm. For example, when a protein is expressed as a fusion protein having an *E. coli*-recognized peptide or "signal peptide" attached to its N-terminus, the desired protein is secreted into the periplasm. Signal peptides that could potentially be employed with the invention are well known in the art and include, for example, those described by Watson (1984), Oka et al, (1985), Hsiung et al, (1986) and EP 177,343, each of the disclosures of which are specifically incorporated herein by reference in their entirety.

In phage display, a gene encoding a protein of interest is commonly linked to the amino-terminal domain of the gene III coat protein of the filamentous phage M13, or another surface-associated molecule. The fusion is mutated to form a library of structurally related fusion proteins that are expressed in low quantity on the surface of phagemid candidates. For example, U.S. Pat. No. 5,571,698 describes directed evolution using an M13 phagemid system. However, in the instant invention, fusion to the gene III coat protein is not necessary, as the protein is expressed in soluble form in the periplasm. Instead, it may be desirable to create a fusion protein of the candidate periplasmic-expressed binding protein or antibody with a signal sequence directing expression of that protein in the periplasm. As such, techniques for the creation of heterogeneous collections of candidate molecules, well known to those of skill in the art in conjunction with phage display, could be adapted for use with the invention. Those of skill in the art will recognize that such adaptations will include the use of bacterial elements for expression and secretion of candidate molecules into the periplasm, including, promoter, enhancers or leader sequences. The current invention provides the advantage relative to phage display of not requiring the creation of fusions with surface-associated molecules, as required in standard display protocols, which may be poorly expressed or may be deleterious to the host cell.

Examples of techniques that could be employed in conjunction with the invention for expression of candidate binding proteins and/or antibodies, in the periplasm include the techniques for expression of immunoglobulin heavy chain libraries described in U.S. Pat. No. 5,824,520. In this technique, a single chain antibody library is generated by creating highly divergent, synthetic hypervariable regions. Similar techniques for antibody display are given by U.S. Pat. No. 5,922,545.

In accordance with another embodiment of the invention, the identification and selection of novel substrates for enzymes also could be carried out in the bacterial periplasm (see, for example, U.S. Pat. No. 5,780,279). The method comprises constructing a gene fusion comprising DNA encoding a polypeptide fused to a DNA encoding a substrate peptide. The DNA encoding the substrate peptide is mutated at one or more codons, thereby generating a family of mutants. The fusion protein could be expressed in the periplasm of a bacterium and subjected to potential inhibition or modification by target ligands. Those bacteria in which modifications have taken place can then be separated from those that have not. By employing FACS screening technology, the general progress of a reaction could similarly be efficiently monitored.

IV. Screening Candidate Molecules

The present invention further comprises methods for identifying molecules capable of binding a target ligand. The molecules screened may comprise large libraries of diverse candidate substances, or, alternatively, may comprise particular classes of compounds selected with an eye towards structural attributes that are believed to make them more likely to bind the target ligand. In a preferred embodiment of the invention, the candidate molecule is an antibody, or a fragment or portion thereof In other embodiments of the invention, the candidate molecule may be another binding protein or an enzyme.

To identify a candidate molecule capable of binding a target ligand in accordance with the invention, one may carry out the steps of: providing a population of Gram negative bacterial cells comprising candidate molecules expressed in the periplasm of the bacteria; admixing the bacteria and at least a first labeled target ligand capable of diffusing into the periplasm of the bacteria; and identifying at least a first bacterium expressing a molecule capable of binding the target ligand.

In the aforementioned method, the binding between the candidate molecule and the ligand will prevent the diffusing out of the cell. In this way, multiple molecules of the labeled ligand will be retained in the periplasm of the bacterium. The labeling may then be used to isolate the cell expressing the molecule capable of binding the target ligand, and in this way, the gene encoding the molecule isolated. The molecule capable of binding the target ligand may then be produced in large quantities using in vivo or ex vivo expression methods, and then used for any desired application, for example, for diagnostic or therapeutic applications, as described below.

As used herein the term "candidate molecule" or "candidate polypeptide" refers to any molecule or polypeptide that may potentially have affinity for a target ligand. The candidate substance may be a protein or fragment thereof, including a small molecule. The candidate molecule may in one embodiment of the invention, comprise an antibody sequence or fragment thereof Such sequences may be particularly designed for the likelihood that they will bind a target ligand.

Binding proteins or antibodies isolated in accordance with the invention also may help ascertain the structure of a target ligand. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for binding the target ligand. Such libraries could be provided by way of nucleic acids encoding the small molecules or bacteria expressing the molecules.

V. Screening of Enzyme Libraries

Yet another aspect of the present invention relates to the isolation of enzyme catalysts capable of catalyzing the conversion of a reaction substrate to a product. The inventors have discovered that a number of fluorescent substrates for enzymatic reactions can permeate into the periplasmic space of E. coli. Cells that express an enzyme capable of reacting with such a substrates produce fluorescent products in direct proportion to the catalytic activity of the protein. The inventors have further found that the fluorescent product of the enzymatic reaction is retained within the cell. As a result, cells become fluorescently stained in proportion to the catalytic activity of the expressed enzyme and can be sorted from a population of mutant proteins by FACS.

Flow cytometry is well suited for the analysis of enzyme activity and kinetics at the single cell level. The inventors have discovered that many fluorescent substrates that normally cannot permeate into the cytoplasm can nonetheless freely diffuse into the periplasm of bacterial cells. Cells expressing an enzyme in the bacterial periplasm are thus capable of converting the substrate into the respective fluorescent product. The inventors further discovered, unexpectedly, that following the enzymatic reaction the fluorescent product is selectively retained within the periplasm and thus the cell becomes fluorescent and can be isolated by FACS.

In the case of the LysoSensor Green DND-189 in the presence of 1 mM 4-nitrophenyl butyrate reaction, it is not a fluorescent product that is being detected. Rather, the LysoSensor Green DND-189 is a pH-sensitive dye, and as the enzyme catalyzes the conversion of 4-nitrophenyl butyrate to 4-nitrophenol and butyric acid in the periplasm, the pH drops in unbuffered solution. This drop in pH is being detected as increased fluorescence by the LysoSensor Green DND-189, which remains associated with the cell via electrostatic attraction. Here, the LysoSensor Green DND-189 becomes protonated at lower pH and thus positively-charged, so it associates with the negatively-charged bacterial outer membrane long enough to allow FACS isolation.

1. Cloning of Binding Protein Coding Sequences

The binding affinity of an antibody or another binding protein can, for example, be determined by the Scatchard analysis of Munson & Pollard (1980). After a bacterial cell is identified that produces molecules of the desired specificity, affinity, and/or activity, the corresponding coding sequence may be cloned. In this manner, DNA encoding the molecule can be isolated and sequenced using conventional procedures (e.g. by using oligonucleotide probes that are capable of binding specifically to genes encoding the antibody or binding protein).

Once isolated, the antibody or binding protein DNA may be placed into expression vectors, which can then transfected into host cells such as simian COS cells, Chinese hamster ovary (CHO) cells, or myeloma cells that do not otherwise produce immunoglobulin protein, to obtain the synthesis of binding protein in the recombinant host cells. The DNA also may be modified, for example, by substituting the coding sequence for human heavy and light chain constant domains in place of the homologous murine sequences (Morrison, et al., 1984), or by covalently joining to the immunoglobulin coding sequence all or part of the coding sequence for a non-immunoglobulin polypeptide. In that manner, "chimeric" or "hybrid" binding proteins are prepared that have the desired binding specificity.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity the target ligand and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

2. Maximization of Protein Affinity for Ligands

In a natural immune response, antibody genes accumulate mutations at a high rate (somatic hypermutation). Some of the changes introduced will confer higher affinity, and B cells displaying high-affinity surface immunoglobulin. This natural process can be mimicked by employing the technique known as "chain shuffling" (Marks et al., 1992). In this method, the affinity of "primary" human antibodies obtained in accordance with the invention could be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large antibody repertoires was described by Waterhouse et al., (1993), and the isolation of a high affinity human antibody directly from such large phage library was reported by Griffith et al., (1994). Gene shuffling also can be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by the phage display technique is replaced with a repertoire of human V domain genes, creating rodent-human chimeras. Selection on the antigen results in isolation of human variable regions capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

3. Labeled Ligands

In one embodiment of the invention, an antibody or binding protein is isolated which has affinity for a labeled ligand. Such a labeled ligand is, in one embodiment of the invention, preferably less that 50,000 Da in size in order to allow efficient diffusion of the ligand into the bacterial periplasm. As indicated above, it will typically be desired in accordance with the invention to provide a ligand which has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels which could be used with the invention include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In a preferred embodiment of the invention, a visually-detectable marker is used such that automated screening of cells for the label can be carried out. In particular, fluorescent labels are preferred in that they allow use of FACS for isolation of cells expressing a desired binding protein or antibody. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging. Types of fluorescent labels that may be used with the invention will be well known to those of skill in the art and include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Examples of paramagnetic ions that could be used as labels include ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts include but are not limited to lanthanum (III), gold (III), lead (II), and especially bismuth (III).

Another type of ligand conjugates contemplated in the present invention are those where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as ligand binding agents.

Labeling can be carried out by any of the techniques well known to those of skill in the art. For instance, ligands can be labeled by contacting the ligand with the desired label and a chemical oxidizing agent such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). Ligands also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

V. Illustrative Use of the Invention

The examples described herein demonstrate the use of the invention for the affinity maturation of the anti-cardiac glycoside scFv 26.10, and the de novo isolation of antibodies from large repertoire libraries. Importantly the current invention results in the isolation of protein variants that are missed by other protein library screening technologies such as phage display. As discussed above, most scFv are toxic to the host cell when targeted to the periplasm. Although reasonable expression levels of such molecules may be obtained by altering culture conditions, provision of chaperones and foldases etc., the host cells are often not recoverable after expression. FACS selection with the anchor-less-display (ALD) techniques of the invention requires a high enough expression level for a strong FACS signal but not so high as to irreversibly damage the cell and prevent its isolation. In contrast, phage display imposes little selection for expression. As a result, proteins isolated from a phage display library screening program are often very difficult to produce in sufficient quantities for further characterization. The advent of highly expressable framework-based libraries (Knappick et al., 2000) should help circumvent the expression versus viability problem. The high sort-rates of current FACS machines generally enable the screening of very large libraries ($10^9$-$10^{10}$) and can completely circumvent phage or cell surface display.

The ability to specifically label periplasmic expressed proteins with appropriate fluorescent ligands also has applications other than library screening. Specifically labeling with fluorescent ligands and flow cytometry can be used for monitoring production during protein manufacturing. While flow cytometry has been used previously for the analysis of bacterial cells, it has not been used for the specific labeling and quantitation of periplasmic proteins. However, a large number of commercially important proteins including IGF-1 several interleukins, enzymes such as urokinase-type plasminogen activator, antibody fragments, inhibitors (e.g., Bovine pancreatic trypsin inhibitor) are expressed in recombinant bacteria in a form secreted into the periplasmic space. The level of production of such proteins within each cell in a culture can be monitored by utilizing an appropriate fluorescent ligand and flow cytometric analysis, according to the techniques taught by the present invention.

Generally, monitoring protein expression requires cell lysis and detection of the protein by immunological techniques or following chromatographic separation. However, ELISA or western blot analysis is time-consuming and does not provide information on the distribution of expression among a cell population and cannot be used for on-line monitoring (Thorstenson et al., 1997; Berrier et al., 2000). In contrast, FACS labeling is rapid and simple and can well be applied to online monitoring of industrial size fermentations of recombinant proteins expressed in gram-negative bacteria. Similarly, the invention could be used to monitor the production of a particular byproduct of a biological reaction. This also could be used to measure the relative concentration or specific activity of an enzyme expressed in vivo in a bacterium or provided ex vivo. The passive and instant nature of ALD provides the advantage of allowing instant analysis of a population of cells with direct observations rather than relying on extensive indirect protocols.

Once a ligand-binding protein, such as an antibody, has been isolated in accordance with the invention, it may be desired to link the molecule to at least one agent to form a conjugate to enhance the utility of that molecule. For example, in order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Techniques for labeling such a molecule are known to those of skill in the art and have been described herein above.

Labeled binding proteins such as antibodies which have been prepared in accordance with the invention may also then be employed, for example, in immunodetection methods for binding, purifying, removing, quantifying and/or otherwise generally detecting biological components such as protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; and De Jager R et al., 1993, each incorporated herein by reference. Such techniques include binding assays such as the various types of enzyme linked immunosorbent assays (ELISAs) and/or radioimmunoassays (RIA) known in the art.

The ligand-binding molecules, including antibodies, prepared in accordance with the present invention may also, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al, 1990).

VI. Automated Screening with FACS

In one embodiment of the invention, fluorescence activated cell sorting (FACS) screening or other automated flow cytometric techniques may be used for the efficient isolation of a bacterial cell comprising a labeled ligand bound to a candidate molecule in the periplasm of the bacteria. Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other methods for flow cytometry can be found in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

VII. Nucleic Acid-Based Expression Systems

Nucleic acid-based expression systems may find use, in certain embodiments of the invention, for the expression of recombinant proteins. For example, one embodiment of the invention involves transformation of Gram negative bacteria with the coding sequences of candidate antibody or other binding proteins having affinity for a selected ligand and the expression of such candidate molecules in the periplasm of the Gram negative bacteria. In other embodiments of the invention, expression of such coding sequences may be carried, for example, in eukaryotic host cells for the preparation of isolated binding proteins having specificity for the target ligand. The isolated protein could then be used in one or more therapeutic or diagnostic applications.

1. Methods of Nucleic Acid Delivery

Certain aspects of the invention may comprise delivery of nucleic acids to target cells. For example, bacterial host cells may be transformed with nucleic acids encoding candidate molecules potentially capable binding a target ligand, In particular embodiments of the invention, it may be desired to target the expression to the periplasm of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into such a cell, or even an organelle thereof Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789, 215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

a. Electroporation

In certain embodiments of the present invention, a nucleic acid is introduced into a cell via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

b. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

2. Vectors

Vectors may find use with the current invention, for example, in the transformation of a gram negative bacterium with a nucleic acid sequence encoding a candidate polypeptide which one wishes to screen for ability to bind a target ligand. In one embodiment of the invention, an entire heterogeneous "library" of nucleic acid sequences encoding target polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example of such promoter that may be used with the invention is the *E. coli* arabinose promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or usefull under the appropriate conditions to direct high level expression of the introduced DNA segment, such as is advantageous in the large-scale production of recombinant proteins and/or peptides. The promoter may be heterologous or endogenous.

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

C. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al, 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

e. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

f. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

3. Host Cells As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a gram negative bacterial cell. These bacteria are suited for use with the invention in that they posses a periplasmic space between the inner and outer membrane. As such, any other cell with such a periplasmic space could be used in accordance with the invention. Examples of Gram negative bacteria that may find use with the invention may include, but are not limited to, E. coli, Pseudomonas aeruginosa, Vibrio cholera, Salmonella typhimurium, Shigella flexneri, Haemophilus influenza, Bordotella pertussi, Erwinia amylovora, Rhizobium sp. The Gram negative bacterial cell may be still further defined as bacterial cell which has been transformed with the coding sequence of a candidate polypeptide capable of binding a selected ligand. The polypeptide will be expressed in the periplasmic space, and may comprise an antibody coding sequence or another sequence. One means for expression of the polypeptide in the periplasm is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials (available on the world wide web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5.alpha., JM109, and KC8, as well as a number of commercially available bacterial hosts such as SURE.RTM. Competent Cells and SOLOPACK.TM. Gold Cells (STRATAGENE.RTM., La Jolla). Alternatively, bacterial cells such as E. coli LE392 could be used as host cells for bacteriophage.

Many host cells from various cell types and organisms are available and would be known to one of skill in the art. Similarly, a viral vector may be used in conjunction with either a eukaryotic or prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Such systems could be used, for example, for the production of a polypeptide product identified in accordance with the invention as capable of binding a particular ligand. Prokaryote- and/or eukaryote-based systems can be employed for use with the present invention to produce nucleic acid sequences, or their cognate polypeptides, proteins and peptides. Many such systems are commercially and widely available.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INITROGEN® which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

5. Candidate Binding Proteins and Antibodies

In certain aspects of the invention, candidate antibodies or other recombinant proteins potentially capable of binding a target ligand are expressed in the periplasm of a host bacterial cell. By expression of a heterogeneous population of such antibodies, those antibodies having a high affinity for a target ligand may be identified. The identified antibodies may then be used in various diagnostic or therapeutic applications, as described herein.

As used herein, the term "antibody" is intended to refer broadly to any immunologic binding agent such as IgG, IgM, IgA, IgD and IgE. The term "antibody" is also used to refer to any antibody-like molecule that has an antigen binding region, and includes antibody fragments such as Fab', Fab, F(ab')$_2$, single domain antibodies (DABs), Fv, scFv (single chain Fv), and engineering multivalent antibody fragments such as dibodies, tribodies and multibodies. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Once an antibody having affinity for a target ligand is identified, the antibody may be purified, if desired, using filtration, centrifugation and various chromatographic methods such as HPLC or affinity chromatography. Fragments of such antibodies can be obtained from the antibodies so produced by methods which include digestion with enzymes, such as pepsin or papain, and/or by cleavage of disulfide bonds by chemical reduction. Alternatively, antibody fragments encompassed by the present invention can be synthesized using an automated peptide synthesizer.

A molecular cloning approach comprises one suitable method for the generation of a heterogeneous population of candidate antibodies that may then be screened in accordance with the invention for affinity to target ligands. In one embodiment of the invention, combinatorial immunoglobulin phagemid can be prepared from RNA isolated from the spleen of an animal. By immunizing an animal with the ligand to be screened, the assay may be targeted to the particular antigen. The advantages of this approach over conventional techniques are that approximately $10^4$ times as many antibodies can be produced and screened in a single round, and that new specificities are generated by H and L chain combination which further increases the chance of finding appropriate antibodies.

VIII. Manipulation and Detection of Nucleic Acids

In certain embodiments of the invention it may be desired to employ one or more techniques for the manipulation and/or detection of nucleic acids. Such techniques may include, for example, the preparation of vectors for transformation of host cells as well as methods for cloning selected nucleic acid segments from a transgenic cells. Methodology for carrying out such manipulations will be well known to those of skill in the art in light of the instant disclosure.

1. Amplification of Nucleic Acids

Nucleic acids used as a template for amplification may be isolated from cells, tissues or other samples according to standard methodologies (Sambrook et al., 1989). In certain embodiments, analysis may be performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety).

European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Oharaet al., 1989).

2. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

3. Kits

All the essential materials and/or reagents required for detecting a target ligand may be provided by the invention and may be assembled together in a kit. This generally will comprise an antibody or binding protein prepared in accordance with the invention and designed to have affinity specifically to a target ligand. Also included may be buffers to provide the necessary mixture for binding to the ligand, as well as labeling means for detecting the binding. Such kits may also include enzymes and other reagents suitable for detection of specific ligands. Such kits generally will comprise, in suitable means, distinct containers for each individual reagent or enzyme as well as for antibody or binding protein.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Fluorescence Detection and Enrichment of Cells Expressing scFv Antibodies in the Periplasm The 26-10 scFv antibody binds with high affinity to cardiac glycosides such as digoxin and digoxigenin ($K_D$ of the purified antibodies for digoxin and digoxigenin are $0.9 \pm 0.2 \times 10^{-1}$ $M^{-1}$ and $2.4 \pm 0.4 \times 10^{-9}$ $M^{-1}$, respectively, Chen et al., 1999). The 26-10 scFv and its variants have been used extensively as a model system to understand the effect of mutations in the CDRs and in the framework regions on hapten binding (Schilbach et al., 1992; Short et al., 1995; Daugherty et al., 1998, 2000; Chen et al., 1999). A derivative of the 26-10 scFv was expressed under the E. coli arabinose promoter and with the pelB leader peptide that allows secretion in the E. coli periplasm. The resulting plasmid vector (pBAD30pelB-Dig) was transformed in the ara E. coli strain LMG194 and protein synthesis was induced with 0.2% w/v arabinose. It was observed that upon incubation with 200 nM of digoxigenin-BODIPY™, cells that had been grown at 25° C. became strongly fluorescent and the fluorescence signal was retained even after extensive washing to remove non-specifically bound ligand. The labeling of the cells with a probe having a M.W. which is significantly higher than the generally accepted size limit of about 600 Da for the permeation of hydrophilic solutes in the periplasm (Decad and Nikaido, 1976) raised the possibility that the fluorescence signal was mainly due to non-viable, permeabilized cells. However, staining with the viability stain propidium iodide, which binds specifically to membrane damaged cells by virtue of intercalating with the normally inaccessible nucleic acids, revealed that >90% of the cells were not permeable to the dye. This is similar to the proportion of intact cells in control E. coli cultures harvested in late exponential phase.

Cells expressing the 26-10 antibody in the periplasm could be enriched from a large excess of E. coli transformed with vector alone in a single round of sorting. Specifically, LMG194 (pBAD30pelB-Dig) were mixed with a 10,000 fold excess of E. coli containing empty vector (pBAD30). The former cells are resistant to both ampicillin and chloramphenicol ($amp^r$, $Cm^r$) whereas the latter are resistant to ampicillin only ($amp^r$). 4 hours after induction with 0.2% w/v arabinose, the cells were then labeled with 100 nM digoxigenin-BODIPY™ for 1 hour and fluorescent cells were isolated by FACS. Following re-growth of the sorted cells and re-labeling as above, the population exhibited a five to eight-fold increase in the mean fluorescence intensity (FL1=20 vs FL1=4 for the pre-sort cell mixture). The fraction of scFv-expressing clones in the enriched population was estimated from the number of ampr clones that were also $Cm^r$. 80% of the ampr colonies were also $Cm^r$ indicating that fluorescence labeling and cell sorting gave an enrichment of well over 1,000-fold in a single round

EXAMPLE 2

Antibody Affinity Maturation

Figure 6A:
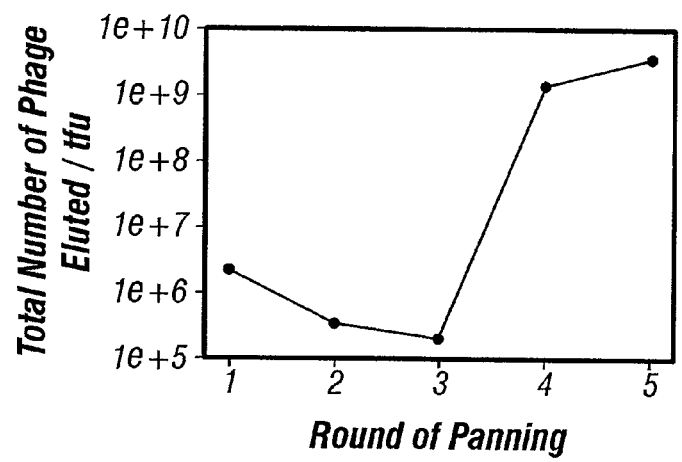
FIGS. 6A-6C.
Figure 6B:
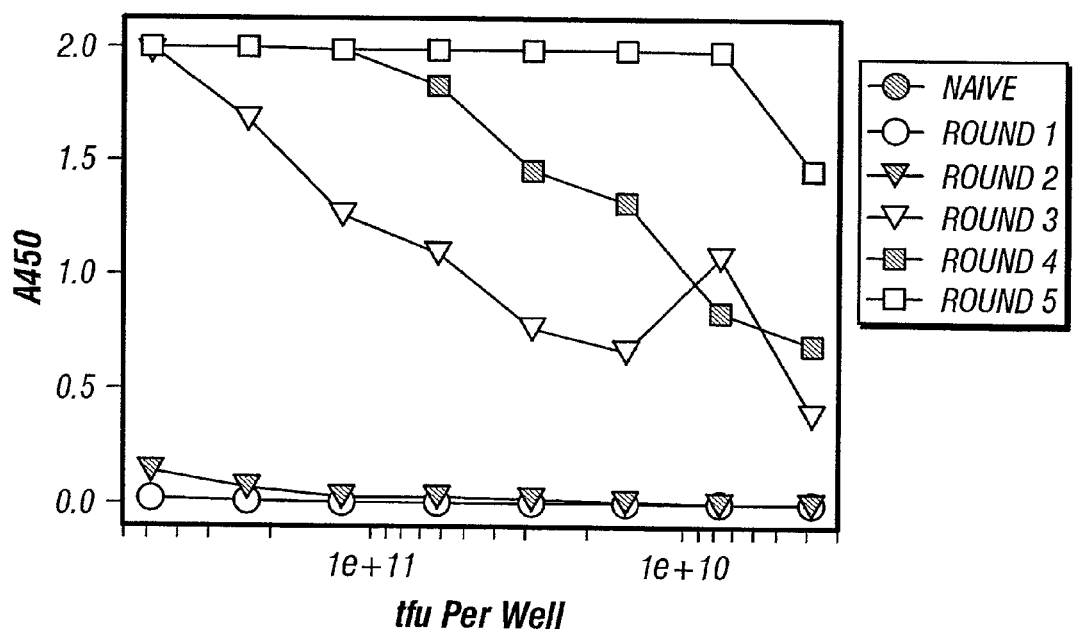

Short et. al., (1995) isolated a 26-10 mutant, designated A4-19, having an equilibrium dissociation constant (KD) for digoxin of 300 pM as measured by surface plasmon resonance. A4-19 contains 3 amino acid substitutions in heavy chain CDR1 ($V_H$:T30->P, $V_H$:D31->S and $V_H$:M34->Y). It was examined whether mutants with increased binding affinity can be obtained by periplasmic expression/FACS screening even when starting with an antibody that already exhibits very tight binding. Three light chain CDR3 residues that make contact ($V_L$:T91, $V_L$:P96) or are in close proximity to ($V_L$:V94) the digoxin hapten (Jeffrey.et al., 1993) were randomized using an NNS (S=G or C) strategy (Daugherty et al. 1998). A library of $2.5 \times 10^6$ transformants expressed in the periplasm via the pelB leader was generated and screened using two rounds of FACS (FIG. 2). In the first round of screening, cells labeled with 100 nM of the fluorescent probe were washed once with PBS and sorted using recovery mode in which the instrument collects all fluorescent events even if a non-fluorescent particle is detected in the same element of fluid as a fluorescent particle. Operation in recovery mode provided a better assurance that very rare cells would be collected but at the expense of purity.

Collected cells were re-grown, labeled, washed and then incubated with a 50-fold excess (50 μM) of free digoxin for various times (15 min to 90 min). Cells that retained the desired level of fluorescence were isolated by sorting using exclusion mode, in which, coincident fluorescent and non-fluorescent events were rejected and thus a higher degree of purity was obtained. The rate of fluorescence decay for the pool of cells obtained following incubation with non-fluorescent competitor for various times was measured. A slightly faster rate compared to the starting A4-19 antibody was observed for the earlier time points (<60 minutes incubation with competitor) but the rate was reduced for the 60 min and 90 min populations. 5 random clones from the cell population obtained after 60 min of competition and 13 clones from the 90 min pool were picked at random and sequenced (Table 1). A strong sequence consensus was clearly evident. The hapten binding kinetics of the purified antibodies were determined by SPR and the results are shown in Table 1. The corresponding amino acid sequences are given by SEQ ID NOs:1-12. It should be noted that upon purification and analysis by gel filtration FPLC none of the mutants was found to dimerize. All of the mutants examined displayed association rate constants ($k_{on}$) indistinguishable from that of the starting A4-19 antibody ($0.9 \pm 0.2 \times 10^6$ $M^{-1}$). The $k_{diss}$ of the clones isolated after 60 min of competition were the same or faster than that of A4-19. Clones isolated after 90 minutes of competition exhibited slower $k_{diss}$ in solution. One clone, 90.3, exhibited a 2-fold slower dissociation rate constant resulting in a $K_D$ of 150 pM. Thus, the library screening methodology of the invention allowed specific labeling to isolate a better mutant, even when starting with an antibody that already exhibited a sub-nanomolar $K_D$. Interestingly, but not surprisingly, the effect of the three heavy chain CDR1 mutations present in 4-19 and the two mutations in residues 94 and 96 of the light chain were additive.

TABLE 1

Heavy and light chain CDR3 amino acid sequences
(SEQ ID NOs: 1-12) of mutants isolated by 60 min
(clones 60.1-60.4 and 90 minutes (clones 90.1-90.6) off-rate selection.

|  | Light Chain Sequence 90 . . . 96 | Off-rate/s |
| --- | --- | --- |
| Wild Type 26-10 scFv | Q T T H V P P | $8.4 \times 10^{-4}$ |
| A14-9 | Q T T H V P P | $2.7 \times 10^{-4}$ |
| 60.1 (1 clone) | Q T T H S P A | $5.5 \times 10^{-4}$ |
| 60.2 (2) | Q T T H L P T | $2.8 \times 10^{-4}$ |
| 60.3 (1) | Q T T H T P P | ND |
| 60.4 (1) | Q T T H L P A | ND |
| 90.1 (1) | Q T T H I P T | $3.2 \times 10^{-4}$ |
| 90.2 (1) | Q T T H V P P | $2.7 \times 10^{-4}$ |
| 90.3 (7) | Q T T H V P A | $2.2 \times 10^{-4}$ |
| 90.4 (1) | Q T T H I P A | $1.4 \times 10^{-4}$ |
| 90.5 (3) | Q T T H L P A | ND |
| 90.6 (1) | Q T T H V P C | ND |

Number of identical clones shown in parenthesis.
ND: Not Determined.

EXAMPLE 3

Maximizing the Fluorescence Signal

The fluorescence intensity of cells expressing scFv antibodies in soluble form in the periplasm was strongly dependent on the E. coli strain used and on the growth conditions. With the 26-10 antibody, the maximum fluorescence intensity was obtained when the cells were grown at 25° C. Growth at sub-physiological temperature has several beneficial effects. Expression of scFv at low temperature (i.e., 25° C.) facilitates the proper folding of the scFv both directly, by slowing the folding pathway and indirectly by decreasing plasmid copy number to reduce expression load. Indeed, direct expression of scFv at 37° C. generally yields little or no soluble protein (for example see Gough et al., 1999). Outer membrane composition is also altered at non-physiological temperatures resulting in increased permeability (Martinez et al., 1999). Rather dramatic differences among various E. coli strains were noticed. Among several strains tested, the highest fluorescence intensities were obtained in ABLE™C (FIG. 3). A preliminary analysis of protein expression and outer membrane protein profile in this strain indicated that the higher fluorescent signal was not due to the pcnB mutation which reduces the copy number of ColE1 origin plasmids but rather, due to differences in cell envelope protein composition. In fact, the stronger staining of ABLE™C was not related to a higher level of protein expression relative to other strains as deduced by ELISA and Western blotting.

Figures 1, 6C:
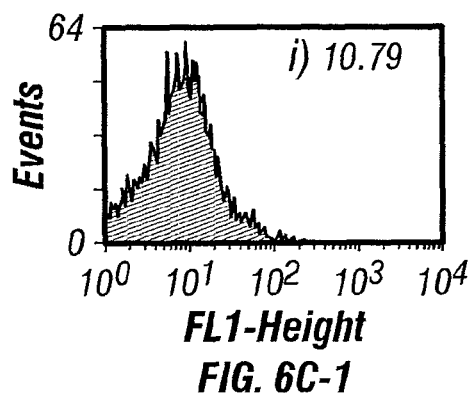
Figures 2, 6C:
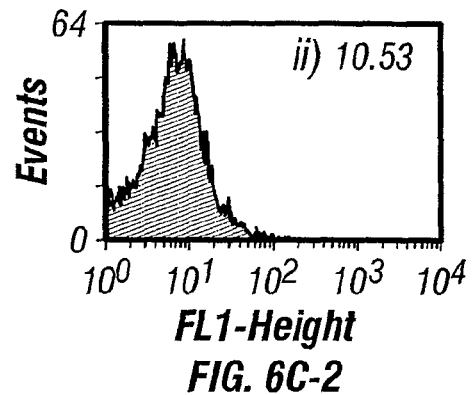
Figures 3, 6C:
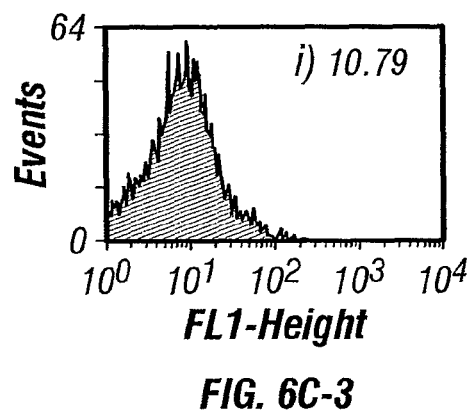
FIG. 3. Shows strain dependence of periplasmic FACS signal: i) TG1/pHEN2.thy; ii) HB2151/pHEN2.thy; iii) ABLE™C/pHEN2.thy; iv) ABLE™K/pHEN2.thy; v) TG1/pHEN2.dig; vi) HB2151/pHEN2.dig; vii) ABLE™C/pHEN2.dig; viii) ABLE™K/pHEN2.dig.
Figures 4, 6C:
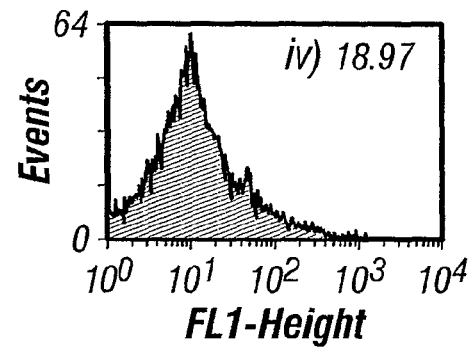
Figures 5, 6C:
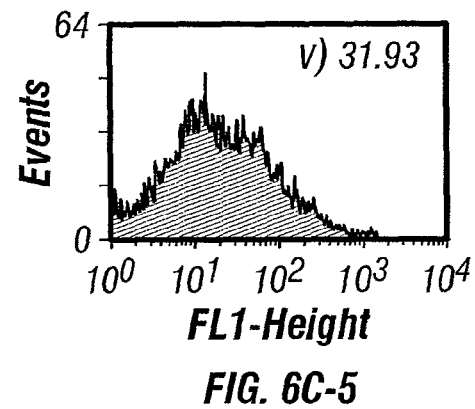
Figures 6, 6C:
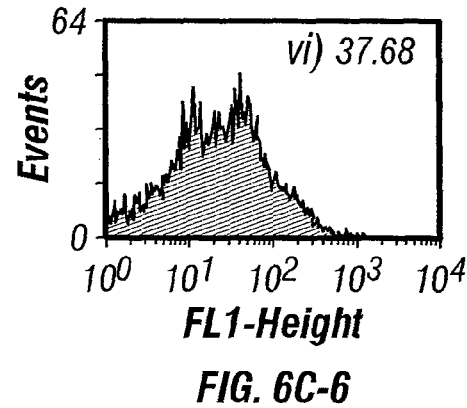

Fluorescent labeling under hyperosmotic conditions, resulted in significantly greater fluorescence (FIG. 4). A 5-7 fold increase in fluorescence was obtained when the cells were incubated in 5× PBS during labeling (a mean FL1>150 compared to 20-30 for cells incubated in regular PBS). However, the increased signal came at a cost, as cell viability decreased considerably. Such a decrease in viability may be undesirable when screening highly diverse libraries of proteins, whose expression may already have a deleterious effect on the host cell. Similarly, co-infection with filamentous phages such as M13KO7 induces the phage shock response, which among other things, results in an increase in outer membrane permeability. M13 KO7 infection resulted in a 3-fold increase in the mean fluorescence of the population (FIG. 5). However, as with hyperosmotic shock the viability of the culture, as determined by propidium iodide staining was somewhat decreased.

Labeling of the cells with fluorescent ligand followed by incubation with a large excess of free ligand results in a time-dependent decrease in the mean fluorescence intensity. The rate of the fluorescence decay reflects the dissociation rate of the antibody-antigen complex (Daugherty et al., 2000). For digoxin the rate of fluorescence decay was found to be about 3-4 times slower compared to the dissociation rate measured with the purified antibody using BIACORE. The lower rate of fluorescence decay compared to the dissociation rate of the antibody/antigen complex in vitro stems from several effects including the collision frequency between ligands and cells, the concentration of antibody in the periplasm and, of course, the rate of diffusion through the outer membrane (see Martinez et al., (1996) for an analysis of kinetics in the periplasmic space). As may be expected, the ratio of the rate of fluorescence decay in the periplasm relative to the in vitro determined $k_{off}$-rate is antigen dependent.

EXAMPLE 4

Analysis and Screening of Repertoire Antibody Libraries by FACS

Antibodies can be isolated de novo, i.e., without animal immunization, by screening large, repertoire libraries that contain a wide variety of antibody sequences. The screening of such large libraries is well established (Nissim et al. 1994, Winter et al. 1994, Griffith et al. 1994, Knappik et al. 2000). It was important to establish: (a) How anchor-less display (ALD) compares with the phage display technology in terms of allowing the isolation of high affinity clones and (b) whether ALD can be used to screen highly diverse libraries.

So far all the large antibody repertoire libraries available have been constructed for use with phage display. The inventors discovered that they could take advantage of the fact that libraries constructed for phage display also allow the expression of proteins within the bacterial periplasmic space. In particular, for low protein copy number display on filamentous bacteriophage, recombinant polypeptides are expressed as N-terminal fusions to pIII. During the course of phage biogenesis, pIII fusions are first targeted to the periplasm and anchored in the inner membrane by a small C-terminal portion of pIII. As phage are released, the scFv-pIII fusion is incorporated alongside wild-type pIII at the terminus of the phage, thereby concluding the assembly process (Rakonjac and Model, 1998; Rakonjac et al., 1999). In the most widely used vectors for phage display an amber codon is placed between the N-terminal scFv and the pIII gene. Thus, in a suitable E. coli suppressor strain, full-length scFv-pIII fusion protein is produced for displaying the scFv whereas in a non-supressor strain only soluble scFv is expressed. The degree of suppression varies with vector and strain but tends to allow only 10% read-through. Thus, as a consequence of the biology of phage display, all amber-codon containing libraries result in a degree of periplasmic expression regardless of host. Hence, it was of great interest to explore whether FACS can aid the isolation of ligand binding proteins from pre-existing, highly diverse, naive libraries (Griffiths et al., 1994; Vaughan et al., 1996; Sheets et al., 1998; Pini et al., 1998; de Haard et al., 1999; Knappik et al., 2000; Sblattero and Bradbury, 2000).

Conventional screening of the phage library by phage panning enriched phage expressing scFvs specific for the cardiac glycoside digoxin (FIG. 6A, B) from a naïve antibody repertoire library. The panning process was performed on a BSA conjugate and the screening was performed on an ovalbumin conjugate to reduce the incidence of protein and hapten-protein interface binders. 24 positive isolates from pan 4 shared the same fingerprint and DNA sequencing of 6 clones confirmed the same heavy and light chain sequence ("dig1") with one of six ("dig2") having a unique HCDR3 and LCDR3 combination (FIG. 7). Repeated screening of the phage library both under identical and under different conditions resulted only in the isolation of clones with the same DNA fingerprint.

FACS analysis of the phage rescued in *E. coli* ABLE™C after each round of panning reveals an increase in mean fluorescence at round 3 which mirrors the phage ELISA signals (FIG. 6C). Significant enrichment of binding clones using a single round of FACS was obtained starting with the population obtained from the $3^{rd}$ round of phage panning. This result is consistent with the enrichment profiles obtained during the course of the panning experiment. FACS screening and sorting 106 cells from rounds 3, 4 and 5 resulted in the isolation of positive clones at a frequency of 30, 80 and 100% respectively.

Out of 14 clones isolated by FACS from the round 3 population 5 were found to be positive for binding to digoxin. Importantly three of the clones corresponded to a different antibody that was missed by phage panning (herein known as "dig3"). The remaining 2 were the dig1 clone. This result demonstrates that FACS screening of libraries expressed in the periplasmic space and labeled with fluorescent ligands results in the isolation of clones that cannot be isolated by other library screening methodologies.

EXAMPLE 5

Materials And Methods

A. Strains and Plasmids

*E. coli* strains TG1 and HB2151 were provided with the Griffin library. ABLE™C and ABLE™K were purchased from Stratagene and helper phage M13K07 from Pharmacia. A positive control for FACS analysis of a phage display vehicle was constructed by replacing a pre-existing scFv in pHEN2 with the 26.10 scFv to create pHEN2.dig. The negative control was pHEN2.thy bearing the anti-thyroglobulin scFv provided with the Griffin.1 library. The $P_{tac}$ vector was a derivative of pIMS120 (Hayhurst, 2000).

B. Phage Panning

The Griffin.1 library is a semi-synthetic scFv library derived from a large repertoire of human heavy and light chains with part or all of the CDR3 loops randomly mutated and recombined in vivo (Griffiths et al., 1994). The library was rescued and subjected to five rounds of panning according to the web-site instruction manual (available on the world wide web at mrc-cpe.cam.ac.uk/.about.phage/gl1p), summarized in Example 6, below. Immunotubes were coated with 10 .mu.gml.sup.-1 digoxin-BSA conjugate and the neutralized eluates were halved and used to infect either TG-1 for the next round of phage panning, or ABLE.TM. C for FACS analysis.

Eluate titers were monitored to indicate enrichment of antigen binding phage. To confirm reactivity, a polyclonal phage ELISA of purified, titer normalized phage stocks arising from each round was performed on digoxin-ovalbumin conjugate. The percentage of positive clones arising in rounds 3, 4 and 5 was established by monoclonal phage ELISA of 96 isolates after each round. A positive was arbitrarily defined as an absorbance greater than 0.5 with a background signal rarely above 0.01. MvaI fingerprinting was applied to 24 positive clones from rounds 3, 4 and 5.

C. FACS screening

An aliquot of phagemid containing, ABLE™C glycerol stock was scraped into 1 ml of 2× TY (2% glucose, 100 µgml⁻ampicillin) to give an OD at 600 nm of approximately 0.1 cm$^{-1}$. After shaking vigorously at 37° C. for 2 h, IPTG was added to 1 mM and the culture shaken at 25° C. for 4 h. 50 µl of culture was labeled with 100 nM BODIPY™-digoxigenin (Daugherty et al., 1999) in 1 ml of 5× PBS for 1 h at room temperature with moderate agitation. For the last 10 min of labeling, propidium iodide was added to 2 µgml$^{-1}$. Cells were pelleted and resuspended in 100 µl of labeling mix. Scanning was performed with Becton-Dickinson FACSort, collecting $10^4$ events at 1500 s$^{-1}$.

For FACS library sorting, the cells were grown in terrific broth and induced with 0.1 mMIPTG. Sorting was performed on $10^6$ events ($10^7$ for round 2) in exclusion mode at 1000 s$^{-1}$. Collected sort liquor was passed through 0.7 µm membrane filters and colonies allowed to grow after placing the filter on top of SOC agar plus appropriate antibiotics at 30° C. for 24 h.

D. Analysis of phage clones

Screening phage particles by ELISA is summarized as follows. Binding of phage in ELISA is detected by primary sheep anti-M13 antisera (CP laboratories or 5 prime-3 prime) followed by a horseradish peroxidase (HRP) conjugated anti-sheep antibody (Sigma). Alternatively, a HRP-anti-M13 conjugate can be used (Pharmacia). Plates can be blocked with 2% MPBS or 3% BSA-PBS. For the polyclonal phage ELISA, the technique is generally as follows: coat MicroTest III flexible assay plates (Falcon) with 100 µl per well of protein antigen. Antigen is normally coated overnight at 4° C. at a concentration of 10-100 µg/ml in either PBS or 50 mM sodium hydrogen carbonate, pH 9.6. Rinse wells 3 times with PBS, by flipping over the ELISA plates to discard excess liquid, and fill well with 2% MPBS or 3% BSA-PBS for 2 hr at 37° C. Rinse wells 3 times with PBS. Add 10 µl PEG precipitated phage from the stored aliquot of phage from the end of each round of selection (about $10^{10}$ tfu.). Make up to 100 µl with 2% MPBS or 3% BSA-PBS. Incubate for 90 min at rt. Discard the test solution and wash three times with PBS-0.05% Tween 20, then 3 times with PBS. Add appropriate dilution of HRP-anti-M13 or sheep anti-M13 antisera in 2% MPBS or 3% BSA-PBS. Incubate for 90 min at rt, and wash three times with PBS-0.05% Tween 20, then 3 times with PBS. If sheep anti-M13 antisera is used, incubate for 90 min at rt, with a suitable dilution of P-anti-sheep antisera in 2% MPBS or 3% BSA and wash three times with PBS-0.05% Tween 20, then 3 times with PBS. Develop with substrate solution (100 µg/ml TMB in 100 mM sodium acetate, pH 6.0, add 10 µl of 30% hydrogen peroxide per 50 ml of this solution directly before use). Add 100 µl to each well and leave at rt for 10 min. A blue color should develop. Stop the reaction by adding 50 µl 1 M sulfuric acid. The color should turn yellow. Read the OD at 450 nm and at 405 nm. Subtract OD 405 from OD 450.

Monoclonal phage ELISA can be summarized as follows. To identify monoclonal phage antibodies the pHEN phage particles need to be rescued: Inoculate individual colonies from the plates in C10 (after each round of selection) into 100 µl 2× TY containing 100 µg/ml ampicillin and 1% glucose in 96-well plates (Corning 'Cell Wells') and grow with shaking (300 rpm.) overnight at 30° C. Use a 96-well transfer device to transfer a small inoculum (about 2 µl) from this plate to a second 96-well plate containing 200 µl of 2× TY containing 100 µg/ml ampicillin and 1% glucose per well. Grow shaking at 37° C. for 1 hr. Make glycerol stocks of the original 96-well plate, by adding glycerol to a final concentration of 15%, and then storing the plates at −70° C. To each well (of the second plate) add VCS-M13 or M13KO7 helper phage to an moi of 10. Stand for 30 min at 37° C. Centrifuge at 1,800 g. for 10 min, then aspirate off the supernatant. Resuspend pellet in 200 µl 2× TY containing 100 µg/ml ampicillin and 50 µg/ml kanamycin. Grow shaking overnight at 30° C. Spin at 1,800 g for 10 min and use 100 µl of the supernatant in phage ELISA as detailed above.

Production of soluble antibody fragments is summarized as follows: the selected pHEN needs to be infected into HB2151 and then induced to give soluble expression of antibody fragments for ELISA. From each selection take 10 µl of eluted phage (about $10^5$ t.u.) and infect 200 µl exponentially growing HB2151 bacteria for 30 min at 37° C. (waterbath). Plate 1, 10, 100 µl, and 1:10 dilution on TYE containing 100 µg/ml ampicillin and 1% glucose. Incubate these plates overnight at 37° C. Pick individual colonies into 100 µl 2× TY containing 100 µg/ml ampicillin and 1% glucose in 96-well plates (Corning 'Cell Wells'), and grow with shaking (300 rpm.) overnight at 37° C. A glycerol stock can be made of this plate, once it has been used to inoculate another plate, by adding glycerol to a final concentration of 15% and storing at −70° C. Use a 96-well transfer device to transfer a small inocula (about 2 µl) from this plate to a second 96-well plate containing 200 µl fresh 2× TY containing 100 µg/ml ampicillin and 0.1% glucose per well. Grow at 37° C., shaking until the OD at 600 nm is approximately 0.9 (about 3 hr). Once the required OD is reached add 25 µl 2× TY containing 100 µg/ml ampicillin and 9 mM IPTG (final concentration 1 mM IPTG). Continue shaking at 30° C. for a further 16 to 24 hr. Coat MicroTest III flexible assay plates (Falcon) with 100 µl per well of protein antigen. Antigen is normally coated overnight at rt at a concentration of 10-100 µg/ml in either PBS or 50 mM sodium hydrogen carbonate, pH 9.6. The next day rinse wells 3 times with PBS, by flipping over the ELISA plates to discard excess liquid, and block with 200 µl per well of 3% BSA-PBS for 2 hr at 37° C. Spin the bacterial plate at 1,800 g for 10 min and add 100 µl of the supernatant (containing the soluble scFv) to the ELISA plate for 1 hr at rt. Discard the test solution and wash three times with PBS. Add 50 µl purified 9E10 antibody (which detects myc-tagged antibody fragments) at a concentration of 4 µg/ml in 1% BSA-PBS and 50 µl of a 1:500 dilution of HRP-anti-mouse antibody in 1% BSA-PBS. Incubate for 60 min at rt, and wash three times with PBS-0.05% Tween 20, then 3 times with PBS. Develop with substrate solution (100 µg/ml TMB in 100 mM sodium acetate, pH 6.0. Add 10 µl of 30% hydrogen peroxide per 50 ml of this solution directly before use). Add 100 µl to each well and leave at rt for 10 min. A blue color should develop. Stop the reaction by adding 50 µl 1 M sulphuric acid. The color should turn yellow. Read the OD at 450 nm and at 405 nm. Subtract OD 405 from OD 450.

Inserts in the library can be screened by PCR screening using the primers designated LMB3: CAG GAA ACA GCT ATG AC (SEQ ID NO:13) and Fd seq1: GAA TTT TCT GTA TGA GG (SEQ ID NO:14). For sequencing of the VH and VL, use is recommend of the primers FOR_LinkSeq: GCC ACC TCC GCC TGA ACC (SEQ ID NO:15) and pHEN-SEQ: CTA TGC GGC CCC ATT CA (SEQ ID NO:16).

EXAMPLE 6

Summary of Methodology for Use of the Griffin.1 Library

Methodology for using the Griffin.1 library can be summarized as follows. The Griffin.1 library is a scFv phagemid library made from synthetic V-gene segments. The library was made by recloning the heavy and light chain variable regions from the lox library vectors (Griffiths et al., EMBO J, 1994) into the phagemid vector pHEN2. A kit for use of the library will contain a tube of the synthetic scFv Library (1 ml), a glycerol stock of the positive control (TG1 containing an anti-thyroglobulin clone), a glycerol stock of the negative control (TG1 containing pHEN2), a glycerol stock of E. coli TG1 (Gibson, 1984) suppressor strain (K12, del(lac-pro), supE, thi, hsdD5/F'traD36, proA+B+, lacIq, lacZdelM15) for propagation of phage particles (the strain supplied is a T-phage resistant variant of this), a glycerol stock of E. coli HB2151 (Carter et al., 1985) and non-suppressor strain (K12, ara, del(lac-pro), thi/F'proA+B+, lacIq, lacZdelM15) for expression of antibody fragments. The library is kept frozen at −70° C. until needed.

The strains are plated and then are grown up as overnight cultures (shaking at 37° C.) of each in 2× TY containing 100 µg/ml ampicillin and 1% glucose. Cultures are diluted 1:100 with 2× TY (2× TY is 16 g Typtone, 10 g Yeast Extract and 5 g NaCl in 1 litre) containing 100 µg/ml ampicillin and 1% glucose and the phagemids rescued by following the procedures described below. A 1:100 mixture is used of positive and the negative control together for one round of selection on immunotubes, coated with thyroglobulin.

The protocol for use of the library is summarized as follows. Phage/phagemid infect F+-E. coli via the sex pili. For sex pili production and efficient infection E. coli must be grown at 37° C. and be in log phase (OD at 600 nm of 0.4-0.6). Throughout the following protocol such a culture is needed. It can be prepared as follows: transfer a bacterial colony from a minimal media plate into 5 ml of 2× TY medium and grow shaking overnight at 37° C. Next day, subculture by diluting 1:100 into fresh 2× TY medium, grow shaking at 37° C. until OD 0.4-0.6 and then infect with phage. A variety of helper phages are available for the rescue of phagemid libraries. VCS-M13 (Stratagene) and M13KO7 (Pharmacia) can be purchased in small aliquots, larger quantities for rescue of phagemid libraries can be prepared as follows: Infect 200 µl E. coli TG1 (or other suitable strain) at OD 0.2 with 10 µl serial dilutions of helper phage (in order to get well separated plaques) at 37° C. (waterbath) without shaking for 30 min. Add to 3 ml molten H-top agar (42° C.) and pour onto warm TYE (note 7) plates. Allow to set and then incubate overnight at 37° C. Pick a small plaque into 3-4 ml of an exponentially growing culture of TG1 (see above). Grow for about 2 hr shaking at 37° C. Inoculate into 500 ml 2× TY in a 2 litre flask and grow as before for 1 hr and then add kanamycin (25 µg/ml in water) to a final concentration of 50-70 µg/ml. Grow for a further 8-16 hr. Spin down bacteria at 10,800 g for 15 min. To the phage supernatant add ⅕ volume PEG/NaCl (20% polyethylene glycol 6000-2.5 M NaCl) and incubate for a minimum of 30 min on ice. Spin 10,800 g for 15 min. Resuspend pellet in 2 ml TE and filter sterilise the stock through a 0.45 µm filter (Minisart NML; Sartorius). Titre the stock and then dilute to about $1 \times 10^{12}$ p.f.u./ml. Store aliquots at −20° C. All spins are performed at 4° C., unless otherwise stated.

For growth of the library, the procedure is summarized as follows: inoculate the whole of the bacterial library stock (about 1×10$^{10}$ clones) into 500 ml 2× TY containing 100 µg/ml ampicillin and 1% glucose. Grow with shaking at 37° C. until the OD at 600 nm is 0.5, this should take about 1.5-2 hours. Infect 25 ml (1×1010 bacteria) from this culture with VCS-M13 or M13KO7 helper phage by adding helper phage in the ratio of 1:20 (number of bacterial cells:helper phage particles, taking into account that 1 OD bacteria at 600 nm=around 8×108 bacteria/ml).

Spin the infected cells at 3,300 g for 10 min. Resuspend the pellet gently in 30 ml of 2× TY containing 100 µg/ml ampicillin and 25 µg/ml kanamycin. Add 470 ml of prewarmed 2× TY containing 100 µg/ml ampicillin and 25 µg/ml kanamycin and incubate shaking at 30° C. overnight. The phage can be concentrated and any soluble antibodies removed (as in TG1 suppression of the amber stop codon encoded at the junction of the antibody gene and gIII is never complete) by precipitating with Polyethylene glycol (PEG) 6000. Spin the culture from A6 at 10,800 g for 10 min (or 3,300 g for 30 min). Add ⅕ volume PEG/NaCl (20% Polyethylene glycol 6000, 2.5 M NaCl) to the supernatant. Mix well and leave for 1 hr or more at 4° C. Spin 10,800 g for 30 min. Resuspend the pellet in 40 ml water and add 8 ml PEG/NaCl. Mix and leave for 20 min or more at 4° C. Spin at 10,800 g for 10 min or 3,300 g for 30 min and then aspirate off the supernatant. Respin briefly and then aspirate off any remaining PEG/NaCl. Resuspend the pellet in 5 ml PBS and spin 11,600 g for 10 min in a microcentrifuge to remove most of the remaining bacterial debris. Store the phage supernatant at 4° C. for short term storage or in PBS, 15% glycerol for longer term storage at −70° C. To titre the phage stock dilute 1 µl phage in 1 ml PBS and use 1 µl of this to infect 1 ml of TG1 at an OD600 0.4-0.6. Plate 50 µl of this, 50 µl of a 1:10$^2$ dilution and 50 µl of a 1:10$^4$ on TYE plates containing 100 µg/ml ampicillin and 1 % glucose and grow overnight at 37° C. Phage stock should be 10$^{12}$-10$^{13}$/ml.

Selection on immunotubes is summarized as follows. Coat Nunc-immunotube (Maxisorp Cat. No. 4-44202) overnight with 4 ml of the required antigen. The efficiency of coating can depend on the antigen concentration, the buffer and the temperature. Usually 10-100 µg/ml antigen in PBS or 50 mM sodium hydrogen carbonate, pH 9.6 at room temperature (rt), is used. Next day wash tube 3 times with PBS (simply pour PBS into the tube and then pour it immediately out again). Fill tube to brim with 2% MPBS. Cover and incubate at 37° C. (or rt according to the stability of antigen) for 2 hr to block. Wash tube 3 times with PBS. Add 10$^{12}$ to 10$^{13}$ cfu. phage, from A13, in 4 ml of 2% MPBS. Incubate for 30 min at rt rotating continuously on an under-and-over turntable and then stand for at least a further 90 min at rt. Throw away the unbound phage in the supernatant. For the first round of selection wash tubes 10 times with PBS containing 0.1% Tween-20, then 10 times with PBS to remove the detergent. Each washing step is performed by pouring buffer in and immediately out. For the second and subsequent rounds of selection wash tubes 20 times with PBS containing 0.1% Tween-20, then 20 times with PBS. Shake out the excess PBS from the tube and elute phage by adding 1 ml 100 mM triethylamine (700 µl triethylamine (7.18 M) in 50 ml water, diluted on day of use) and rotating continuously for 10 min on an under-and-over turntable. During the incubation, tubes are prepared with 0.5 ml 1M Tris, pH 7.4 ready to add the eluted 1 ml phage, from 7, for quick neutralisation. Phage can be stored at 4° C. or used to infect TG1 as described above. After elution add another 200 µl of 1M Tris, pH 7.4 to the immunotube to neutralise the remaining phage in the tube. Take 9.25 ml of an exponentially growing culture of TG1 and add 0.75 ml of the eluted phage.

Also add 4 ml of the TG1 culture to the immunotube. Incubate both cultures for 30 min at 37° C. (waterbath) without shaking to allow for infection. Pool the 10 ml and 4 ml of the infected TG1 bacteria and take 100 µl to make 4-5 100-fold serial dilutions. Plate these dilutions on TYE containing 100 µg/ml ampicillin and 1% glucose. Grow overnight at 37° C. Take the remaining infected TG1 culture and spin at 3,300 g for 10 min. Resuspend the pelleted bacteria in 1 ml of 2× TY and plate on a large Nunc Bio-Assay dish (Gibco-BRL (note 8)) of TYE containing 100 µg/ml ampicillin and 1% glucose. Grow at 30° C. overnight, or until colonies are visible.

For further rounds of selection, add 5-6 ml of 2× TY, 15% glycerol to the Bio-Assay dish of cells and loosen the cells with a glass spreader. After inoculating 50-100 µl of the scraped bacteria to 100 ml of 2× TY containing 100 µg/ml ampicillin and 1% glucose, store the remaining bacteria at −70° C. Once again it is a good idea to check starting OD at 600 nm is=<0.1. Grow the bacteria with shaking at 37° C. until the OD at 600 nm is 0.5 (about 2 hr). Infect 10 ml of this culture with VCS-M13 or M13KO7 helper phage by adding helper phage in the ratio of 1:20 (number of bacterial cells: helper phage particles, taking into account that 1 OD bacteria at 600 nm=around 8×108 bacteria/ml). Incubate without shaking in a 37° C. water bath for 30 min. Spin the infected cells at 3,300 g for 10 min. Resuspend the pellet gently in 50 ml of 2× TY containing 100 µg/ml ampicillin and 25 µg/ml kanamycin and incubate shaking at 30° C. overnight. Take 40 ml of the overnight culture and spin at 10,800 g for 10 min or 3,300 g for 30 min. Add ⅕ volume (8 ml) PEG/NaCl (20% Polyethylene glycol 6000, 2.5 M NaCl) to the supernatant. Mix well and leave for 1 hr or more at 4° C. Spin 10,800 g for 10 min or 3,300 g for 30 min and then aspirate off the supernatant. Respin briefly and then aspirate off any remaining dregs of PEG/NaCl. Resuspend the pellet in 2 ml PBS and spin 11,600 g for 10 min in a micro centrifuge to remove most of the remaining bacterial debris. 1 ml of this phage can be stored at 4° C. and the other 1 ml aliquot can be used for the next round of selection. Repeat the selection for another 2-3 rounds.

Screening phage particles by ELISA is summarized as follows. Binding of phage in ELISA is detected by primary sheep anti-M13 antisera (CP laboratories or 5 prime-3 prime) followed by a horseradish peroxidase (HRP) conjugated anti-sheep antibody (Sigma). Alternatively, a HRP-anti-M13 conjugate can be used (Pharmacia). Plates can be blocked with 2% MPBS or 3% BSA-PBS. For the polyclonal phage ELISA, the technique is generally as follows: coat MicroTest III flexible assay plates (Falcon) with 100 µl per well of protein antigen. Antigen is normally coated overnight at rt at a concentration of 10-100 µg/ml in either PBS or 50 mM sodium hydrogen carbonate, pH 9.6. Rinse wells 3 times with PBS, by flipping over the ELISA plates to discard excess liquid, and block with 200 µl per well of 2% MPBS or 3% BSA-PBS for 2 hr at 37° C. Rinse wells 3 times with PBS. Add 10 µl PEG precipitated phage from the stored aliquot of phage from the end of each round of selection (about 10$^{10}$ cfu.). Make up to 100 µl with 2% MPBS or 3% BSA-PBS. Incubate for 90 min at rt. Discard the test solution and wash three times with PBS-0.05% Tween 20, then 3 times with PBS. Add appropriate dilution of HRP-anti-M13 or sheep anti-M13 antisera in 2% MPBS or 3% BSA-PBS. Incubate for 90 min at rt, and wash three times with PBS-0.05% Tween 20, then 3 times with PBS. If sheep anti-M13 antisera is used, incubate for 90 min at rt, with a suitable dilution of HRP-anti-sheep antisera in 2% MPBS or 3% BSA and wash three times with PBS-0.05% Tween 20, then 3 times with PBS. Develop with substrate solution (100 µg/ml TMB in 100 mM sodium acetate, pH 6.0. Add 10 µl of 30% hydrogen peroxide per 50 ml of this solution directly before use). Add 100 µl to each well and leave at rt for 10 min. A blue colour should develop. Stop the reaction by adding 50 µl 1 M sulphuric acid. The colour should turn yellow. Read the OD at 450 nm and at 405 nm. Subtract OD 405 from OD 450.

Monoclonal phage ELISA can be summarized as follows. To identify monoclonal phage antibodies the pHEN phage particles need to be rescued: Inoculate individual colonies from the plates in C10 (after each round of selection) into 100 µl 2× TY containing 100 µg/ml ampicillin and 1% glucose in 96-well plates (Corning 'Cell Wells') and grow with shaking (300 rpm.) overnight at 37° C. Use a 96-well transfer device to transfer a small inoculum (about 2 µl) from this plate to a second 96-well plate containing 200 µl of 2× TY containing 100 µg/ml ampicillin and 1% glucose per well. Grow shaking at 37° C. for 1 hr. Make glycerol stocks of the original 96-well plate, by adding glycerol to a final concentration of 15%, and then storing the plates at −70° C. To each well (of the second plate) add 25 µl 2× TY containing 100 µg/ml ampicillin, 1% glucose and 109 pfu VCS-M13 or M13KO7 helper phage. Stand for 30 min at 37° C., then shake for 1 hr at 37° C. Spin 1,800 g. for 10 min, then aspirate off the supernatant. Resuspend pellet in 200 µl 2× TY containing 100 µg/ml ampicillin and 50 µg/ml kanamycin. Grow shaking overnight at 30° C. Spin at 1,800 g for 10 min and use 100 µl of the supernatant in phage ELISA as detailed above.

Production of soluble antibody fragments is summarized as follows: the selected pHEN needs to be infected into HB2151 and then induced to give soluble expression of antibody fragments for ELISA. From each selection take 10 µl of eluted phage (about 105 t.u.) and infect 200 µl exponentially growing HB2151 bacteria for 30 min at 37° C. (waterbath). Plate 1, 10, 100 µl, and 1:10 dilution on TYE containing 100 µg/ml ampicillin and 1% glucose. Incubate these plates overnight at 37° C. Pick individual colonies into 100 µl 2× TY containing 100 µg/ml ampicillin and 1% glucose in 96-well plates (Corning 'Cell Wells'), and grow with shaking (300 rpm.) overnight at 37° C. A glycerol stock can be made of this plate, once it has been used to inoculate another plate, by adding glycerol to a final concentration of 15% and storing at −70° C. Use a 96-well transfer device to transfer a small inocula (about 2 µl) from this plate to a second 96-well plate containing 200 µl fresh 2× TY containing 100 µg/ml ampicillin and 0.1% glucose per well. Grow at 37° C., shaking until the OD at 600 nm is approximately 0.9 (about 3 hr). Once the required OD is reached add 25 µl 2× TY containing 100 µg/ml ampicillin and 9 mM IPTG (final concentration 1 mM IPTG). Continue shaking at 30° C. for a further 16 to 24 hr. Coat MicroTest III flexible assay plates (Falcon) with 100 µl per well of protein antigen. Antigen is normally coated overnight at rt at a concentration of 10-100 µg/ml in either PBS or 50 mM sodium hydrogen carbonate, pH 9.6. The next day rinse wells 3 times with PBS, by flipping over the ELISA plates to discard excess liquid, and block with 200 µl per well of 3% BSA-PBS. for 2 hr at 37° C. Spin the bacterial plate at 1,800 g for 10 min and add 100 µl of the supernatant (containing the soluble scFv) to the ELISA plate for 1 hr at rt. Discard the test solution and wash three times with PBS. Add 50 µl purified 9E10 antibody (which detects myc-tagged antibody fragments) at a concentration of 4 µg/ml in 1% BSA-PBS and 50 µl of a 1:500 dilution of HRP-anti-mouse antibody in 1% BSA-PBS. Incubate for 60 min at rt, and wash three times with PBS-0.05% Tween 20, then 3 times with PBS. Develop with substrate solution (100 µg/ml TMB in 100 mM sodium acetate, pH 6.0. Add 10 µl of 30% hydrogen peroxide per 50 ml of this solution directly before use). Add 100 µl to each well and leave at rt for 10 min. A blue colour should develop. Stop the reaction by adding 50 µl 1 M sulphuric acid. The colour should turn yellow. Read the OD at 450 nm and at 405 nm. Subtract OD 405 from OD 450.

Inserts in the library can be screened by PCR screening using the primers designated LMB3: CAG GAA ACA GCT ATG AC (SEQ ID NO:13) and Fd seq1: GAA TTT TCT GTA TGA GG (SEQ ID NO:14). For sequencing of the VH and VL, use is recommend of the primers FOR_LinkSeq: GCC ACC TCC GCC TGA ACC (SEQ ID NO:15) and pHEN-SEQ: CTA TGC GGC CCC ATT CA (SEQ ID NO:16).

EXAMPLE 7

Isolation of scFV Antibodies Specific to TNB from a Repertoire Library

This example summarizes the screening of a repertoire antibody library to the ligand TNB (trinitrobenzene). Library screening was initiated by first carrying out three rounds of phage panning of a repertoire library (Griffin-1 library) using standard protocols (see example 6, also described in available on the world wide web at mrc-cpe. cam.ac.u/ld.about.phage/glp). Phage rescued from various rounds of panning were used to infect the *E. coli* ABLE C. The cells were grown to mid-exponential phase, induced for expression of scFv antibodies as described above and labeled with 100 nM TNBS conjugated to the fluorescent dye Cy5. The labeled cells were analyzed by flow cytometry using a Cytomation MoFlo instrument equipped with a 5 mM diode laser emitting at 633 nm. Highly fluorescent clones were isolated on membrane filters and analyzed further. Three out of 10 clones isolated by FACS were analyzed further and found to exhibit strong binding to a TNBS-BSA conjugate. Sequence analysis confirmed that one of the TNBS specific clones had also been found by phage display. However, the two other clones isolated by the present invention (periplasmic expression of the library and FACS screening) did not correspond to any of the clones isolated by phage panning.

EXAMPLE 8

Detection of Oligonucleotide Probes by Antibodies Expressed in the *E. coli* Periplasm This example shows that modified oligonucleotides can diffuse through the outer membrane of bacteria. An oligonucleotide with the sequence 5'-digoxigenin-AAAAA-fluoroscein-3' (designated dig-5A-FL, molecular weight of 2,384 Da, SEQ ID NO:22) containing four nuclease resistant phosphorothioate linkages between the five A residues was synthesized and purified (RP HPLC) by Integrated DNA Technologies, IA. The digoxigenin moiety of this oligonucleotide can be recognized by scFv antibodies specific to digoxin (anti-digoxin scFv). Cells expressing the anti-digoxin scFv in the periplasm may bind 5A-Fl which in turn should render the cells fluorescent, provided that the probe molecule can diffuse through the outer membrane.

ABLE™C cells expressing periplasmic scFv specific for either atrazine (Hayhurst 2000) as a negative control (FIG. 8, panels i and iii) or digoxigenin (FIG. 8, panels ii and iv) were incubated in 5× strength PBS (see example 3) together with either 100 nM of digoxigenin-BODIPY™ or 100 nM of dig-5A-FL. Propidium iodine was also added to serve as a viability stain. Viable cells were gated on the basis of propidium iodine exclusion (to identify cells with an intact membrane) and side scatter. Approximately 10,000 cells were analyzed at a rate of 1,000 events per second. The resulting data are shown in FIG. 8. Cells expressing an unrelated anti-atrazine antibody that does not bind to the probe exhibited only background fluorescence. In contrast, cells displaying the anti-digoxin scFv antibody became clearly labeled with both the digoxigenin-BODIPY™ as well as with 5-A-FL. The latter probe gave a signal that was clearly higher than that observed with the control cells. Even though 5-A-FL gave a lower fluorescence intensity compared to the smaller and uncharged the digoxigenin-BODIPY, the signal obtained with the former probe was sufficient for the screening of scFv libraries by FACS.

EXAMPLE 9

Flow Cytometric Discrimination of *E. coli* Expressing the *Fusarium solani* Lipase Cutinase Using Commercial Fluorescent Substrates This example demonstrates that commercially available fluorescent substrates can be used to specifically label *E. coli* cells displaying the relevant enzymes in their periplasm. Surprisingly, the fluorescent product of these reactions is sufficiently retained within the cell to allow for the discrimination and selection of enzyme expressing *E. coli* from non-enzyme expressing bacteria.

The gene encoding *Fusarium solani* lipase cutinase was constructed by total gene synthesis and placed downstream of the strong inducible promoter pBAD in plasmid pBAD18Cm. Protein expression from the pBAD promoter is beneficial for the screening of protein libraries by FACS (Daugherty et al. 1999). The resulting plasmid encoding the cutinase gene was designated pKG3-53-1. pKG3-53-1, and pBAD18Cm as a control, were both transformed into DH5a. In this example, the ability to discriminate cells expressing cutinase (DH5a (pKG3-53-1)) from control cells was determined using two different commercially available substrates: Fluorescein dibutyrate or LysoSensor Green DND-189 (LSG) (both from Molecular Probes, OR). The latter is a positively charged fluorescent probe that detects pH changes in the cell occurring due to ester hydrolysis by the enzyme.

Cells were grown overnight with vigorous shaking at 37° C. in terrific broth/chloramphenicol 50 µg/ml (TB/Cm). Subcultures were made from 100 µl of overnight culture in 10 ml of TB/Cm(50 µg/ml). These subcultures were grown with vigorous shaking at 37° C. to $OD_{600}$=0.6. Four ml aliquots of the subcultures were pelleted at 3650 rpm for 20 minutes in a Beckman Allegra 6R Centrifuge. The supernatant was removed, and the pellets were resuspended in 4 ml of M9 minimal media containing 0.2% glucose and chloramphenicol (Cm) at 50 µg/ml. Arabinose, from a 20% stock, was added to a final concentration of 0.2%. The cultures were induced at 25° C. with vigorous shaking for 4 hours. Subsequently, 2 ml aliquots of the induced cultures were pelleted at 8000 rpm for 10 minutes in an Eppendorf 5415C Centrifuge, washed with fresh media and pelleted again at 8000 rpm for 10 min. The washed pellets were resuspended in M9 salts media without glucose to an optical density $OD_{600}$=1.0. The stock solution was diluted 1:10 and 1 ml of the diluted cell suspension was mixed with 0.1 ml 0.1 mM Fluorescein dibutyrate (FDB) stock solution in dimethyl sulfoxide (DMSO). The final FDB concentration was 10 µM. Reactions were allowed to proceed at 37° C. for 30 minutes. The labeled cells were immediately analyzed on a Becton Dickinson FACSort equipped with an Ar 488 nm laser. The fluorescence distribution of the cutinase expressing cells and the control cells is shown in FIG. 9A.

The utility of a second probe for the discrimination between positive (enzyme expressing) and control cells was also examined. *E. coli* expressing cutinase from the pKG3-53-4 plasmid, and negative cells (expressing the unmodified pBAD18Cm plasmid) were grown, induced and washed as above. The pellet was washed with 1% sucrose, pelleted again, and resuspended in fresh 1% sucrose to $OD_{600}$=1.0. This stock solution of cells was kept on ice.

For labeling, a LysoSensor Green DND-189 (LSG, Molecular Probes) stock solution was prepared to 1 mM in DMSO. Also, a 1 M 4-Nitrophenyl Butyrate stock solution was prepared in DMSO. Cell labeling was initiated by first diluting the cell stock solution, adding the LSG to a final concentration of 1 µM and diluting the 4-Nitrophenyl Butyrate 1:1000 to give a final concentration of 1 µM. The enzymatic hydrolysis of 4-Nitrophenyl Butyrate by the cells was allowed to proceed at 25° C. for 5 minutes and the cells were then immediately analyzed on a Becton Dickinson FACSort as above. The fluorescence distribution of the cutinase expressing cells and the control cells stained with the LysoSensor Green DND-189 probe is shown in FIG. 9B.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Am J Pediatr Hematol Oncol*, 12(4):480-9, 1990.
Almendro et al., *J Immunol*. 157:5411, 1996
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Atherton et al., *Biol. of Reproduction*, 32:155, 1985.
Banerji et al., *Cell*, 27:299, 1981.
Banerji et al., *Cell*, 35:729, 1983.
Bellus, *J. Macromol. Sci. Pure Appl. Chem.*, RS3241(1): 1355-1376, 1994.
Berberian et al., *Science*, 261:1588-1591, 1993.
Berkhout et al., *Cell*, 59:273, 1989.
Berrier et al., *J. Bacteriol.*, 182:248, 2000.
Blanar et al., *EMBO J.*, 8:1139, 1989.
Bodine and Ley, *EMBO J.*, 6:2997, 1987.
Boeke et al, *Mol. Gen. Genet.*, 186: 1982.
Boshart et al., *Cell*,. 41:521, 1985.
Bosze et al, *EMBO J.*, 5:1615, 1986.
Braddock et al., *Cell*, 58:269, 1989.
Bukau et al., *J. Bacteriol.*, 163:61, 1985.
Bulla and Siddiqui, *J. Virol.*, 62:1437, 1986.
Burioni et al., *Res. Virol.*, 149:327, 1998.

Burman et al., *J. Bacteriol.*, 112:1364, 1972.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carter et al., *Nucleic Acids Res* 13:4431, 1985.
Celander and Haseltine, J Virology, 61:269, 1987.
Celander et al., *J. Virology*, 62:1314, 1988.
Chandler et al., Cell, 33:489, 1983.
Chang et al., *MoL Cell. Biol.*, 9:2153, 1989.
Chatterjee et al., *Proc. Nat'l Acad. Sci. USA.*, 86:9114, 1989.
Chen et al., *J. Mol. Biol.*, 293:865, 1999.
Choi et al., *Cell*, 53:519, 1988.
Chowdhury and Pastan, Nat. Biotech., 17:568, 1999.
Cleary et al., Trends Microbiol., 4:131-136, 1994.
Coffin, In: *Virology*, ed., New York: Raven Press, pp. 1437-1500, 1990.
Cohen et al., *Proc. Nat'l Acad. Sci. USA* 75:472, 1987.
Coia et al., *Gene* 201:203, 1997.
Corey et al., *Gene*, 128:129, 1993.
Costa et al., Mol. Cell. Biol., 8:81, 1988.
Cripe et al., EAMBO J, 6:3745, 1987.
Culotta and Hamer, Mol. Cell. Biol., 9:1376, 1989.
Dall'Acqua and Carter, Curr. Opin. Struct. Biol., 8:443, 1998.
Dandolo et al., *J. Virology*, 47:55, 1983.
Daugherty et al., *J. Immunol. Methods.* 243:211, 2000.
Daugherty et al., *Prot. Eng.* 12:613, 1999.
Daugherty et al., *Prot. Eng.*, 111:825, 1998.
De Haard et al., *J. BioL Chem.*, 274:18218, 1999.
De Jager R et al., *Semin Nucl Med* 23:165, 1993.
De Villiers et al., *Nature*, 312:242, 1984.
De Wildt et al., *Nat. Biotechnol.* 18:, 989, 2000.
Decad and Nikaido, *J. Bacteriol.*, 128:325, 1976.
Deng et al., *J. Biol. Chem.*, 269:9533, 1994.
Deng et al., *Proc. Natl. Acad Sci. USA.* 92:4992, 1995.
Deschamps et al., *Science*, 230:1174, 1985.
Dholakia et al., J. Biol. Chem., 264, 20638-20642, 1989.
Doolittle M H and Ben-Zeev O, *Methods Mol Biol.*, 109:215, 1999.
Duenas and Borrebaeck, *Biotechnology*, 12:999, 1994.
Edbrooke et al., *Mol. Cell. Biol.*, 9:1908, 1989.
Edlund et al., *Science*, 230:912, 1985.
Farmer et al., *FEMS Microbiol. Lett.*, 176:11, 1999.
Feng and Holland, *Nature*, 334:6178, 1988.
Firak and Subramanian, *Mol. Cell. Biol.*, 6:3667, 1986.
Frohman, In: *PCR PROTOCOLS: A GUIDE TO METHODS AND APPLICATIONS*, Academic Press, N.Y., 1990.
Fujita et al., *Cell*, 49:357, 1987.
Georgiou et al., *Nat. Biotechnol.* 15:29, 1997.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Nat'l Acad. Sci. USA,* 85:1447, 1988.
Goodbourn et al., *Cell*, 45:601, 1986.
Gough et al., *J. Immunol. Met.*, 228:97, 1999.
Greene et al., *Immunology Today*, 10:272, 1989.
Griep et al., *Prot. Exp. Purif.*, 16:63, 1999.
Griffiths et al., *EMBO J.*, 13: 3245, 1994.
Grosschedl and Baltimore, *Cell*, 41:885, 1985.
Gulbis and Galand, *Hum Pathol* 24:1271, 1993.
Haslinger and Karin, *Proc. Nat'l Acad. Sci. USA.*, 82:8572, 1985.
Hauber and Cullen, *J. Virology*, 62:673, 1988.
Hawkins et al., *J. Mol. Biol.*, 226:889, 1992.
Hayhurst, Prot. Exp. Purif., 18:1, 2000.
Hearing et al., *J. Virol.*, 67:2555-2558, 1987.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10: 1959, 1990.
Hobot et al., *J. Bacteriol.* 160:143, 1984.
Holbrook et al., *Virology*, 157:211, 1987.
Hoogenboom et al., *Adv. Drug. Deliv. Rev.*, 31:5, 1998.
Horlick and Benfield, *Mol Cell. Biol.*, 9:2396, 1989.
Hsiung et al, *Biotechnology*, 4:991, 1994.
Huang et al., *Cell*, 27:245, 1981.
Hudson, Curr. Opin. Biotechnol., 9:395, 1998.
Hwang et al., *MoL Cell. Biol.*, 10: 585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA.* 85:9436, 1988.
Irvin et al., *J. Bacteriol.*, 145:1397, 1981.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jeffrey et al., *Proc. Natl. Acad. Sci. USA.* 90:10310, 1993.
Johns et al., *J. Immunol. Methods*, 239:137, 2000.
Johnson et al., *Mol. Cell. Biol.*, 9:3393, 1989.
Jouenne and Junter, FEMS Microbiol. Lett., 56:313, 1990.
Kadesch and Berg, *Mol. Cell. Biol.*, 6:2593, 1986.
Kang et al., *Science*, 240:1034-1036, 1988.
Karin et al., *Mol. Cell. Biol.*, 7:606, 1987.
Katinka et al., *Cell*, 20:393, 1980.
Katinka et al., *Nature*, 290:720, 1981.
Kawamoto et al., *Mol. Cell. Biol.*, 8:267, 1988.
Khatoon et al., Ann. of Neurology, 26, 210-219, 1989.
Kiledjian et al., *Mol. Cell. Biol.*, 8:145, 1988.
King et al., *J. BioL Chem.*, 269:10218, 1989.
Kjaer et al., FEBS Lett., 431:448, 1998.
Klamut et al., *Mol. Cell. Biol.*, 10:193, 1990.
Knappick et al., *J. Mol. Biol.*, 296:57, 2000.
Koch et al., *Mol. Cell. Biol.*, 9:303, 1989.
Kohler et al., *Methods Enzymol.*, 178:3, 1989.
Kraus et al., *FEBS Lett.*, 428:165, 1998.
Krebber et al., *Gene*, 178:71, 1996.
Krebber et al., *J. Immunol. Methods*, 201:35, 1997.
Kreier et al., Infection, Resistance and Immunity, Harper & Row, New York, (1991)).
Kriegler and Botchan, In: *Eukaryotic Viral Vectors*, Y. Gluzman, ed., Cold Spring Harbor: Cold Spring Harbor Laboratory, NY, 1982.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., In: *Gene Expression*, D. Hamer and M. Rosenberg, eds., New York: Alan R. Liss, 1983.
Kuhl et al., *Cell*, 50:1057, 1987.
Kunz et al., *Nucl. Acids Res.*, 17:1121, 1989.
Kwoh et al., *Proc Natl Acad Sci USA.* 86:1173, 1989.
Labischinski et al., *J. Bacteriol.*, 162:9, 1985.
Lareyre et al., *J Biol Chem.*, 274:8282, 1999.
Larsen et al., *Proc. Nat'l Acad. Sci. USA.*, 83:8283, 1986.
Laspia et al., *Cell*, 59:283, 1989.
Latimer et al., *Mol. Cell. Biol.*, 10:760, 1990.
Lee et al., *J Auton Nerv Syst.* 74:86, 1997
Lee et al., *Nature*, 294:228, 1981.

Lenert et al., *Science*, 248:1639-1643, 1990.
Levinson et al., *Nature*, 295:79, 1982.
Levitan, *J. Mol. Biol.*, 277:893, 1998.
Lin et al., *Mol. Cell. Biol.*, 10:850, 1990.
Luria et al., *EMBO J.*, 6:3307, 1987.
Lusky and Botchan, *Proc. Nat'l Acad. Sci. USA.*, 83:3609, 1986.
Lusky et al., *Mol. Cell. Biol.*, 3:1108, 1983.
MacKenzie and To, *J. Immunol. Methods*, 220:39, 1998.
MacKenzie et al., *J. Biol. Chem.*, 271:1527, 1996.
Maenaka et al., *Biochem Biophys Res Commun.*, 218:682, 1996.
Majors and Varmus, *Proc. Nat'l Acad. Sci. USA.*, 80:5866, 1983.
Malmborg et al., *J. Immunol. Methods*, 198:51, 1996.
Marciano et al., *Science* 284:1516, 1999.
Marks et al., *Bio/Technol.* 10:779, 1992.
Marks et al., *J. Mol. Biol.*, 222:581, 1991.
Martinez et al., *Biochemistry*, 35:1179, 1996.
Martinez et al., *J. Biotechnol.*, 71:59, 1999.
McNeall et al., *Gene*, 76:81, 1989.
Miksicek et al., *Cell*, 46:203, 1986.
Mitchell et al., *Ann. N.Y. Acad. Sci.*, 690:153, 1993.
Mordacq and Linzer, *Genes and Dev.*, 3:760, 1989.
Moreau et al., *Nucl. Acids Res.*, 9:6047, 1981.
Morrison, et al., *Proc. Nat'l. Acad. Sci USA.* 81:6851, 1984.
Muesing et al., *Cell*, 48:691, 1987.
Munson & Pollard, Anal. Biochem. 107:220, 1980.
Mutuberria et al., *J. Immunol. Methods*, 231:65, 1999.
Nakae, *J. Biol. Chem.*, 251:2176, 1976.
Nikaido and Nakae, *Adv. Microb. Physiol.*, 20:163, 1979.
Nikaido and Vaara, *Microbiol. Rev.* 49:1, 1985.
Nissim et al., *EMBO J.*, 13:692, 1994.
Nomoto et al., *Gene*, 236:259, 1999.
Ohara et al., "One-sided polymerase chain reaction: the amplification of cDNA,"
Oka et al., Proc. Natl. Acad. Sci. U.S.A., Vol 82, pp 7212-7216, November 1985
O'Shannessy et al., *J. Immun. Meth.*, 99, 153-161, 1987.
Owens & Haley, J. Biol. Chem., 259:14843-14848, 1987.
Painbeni et al., *Proc Natl. Acad Sci. USA*, 94:6712, 1997.
Palmiter et al., *Nature*, 300:611, 1982.
Pech et al., *Mol. Cell. Biol.*, 9:396, 1989.
Perez-Stable and Constantini, *Mol. Cell. Biol.*, 10:11 16, 1990.
Picard and Schaffner, *Nature*, 307:83, 1984.
Pini et al., *J. Biol. Chem.*, 273:21769, 1998.
Pinkert et al., *Genes and Dev.*, 1:268, 1987.
Ponta et al., *Proc. Nat'l Acad. Sci. USA.*, 82:1020, 1985.
Porton et al., *Mol. Cell. Biol.*, 10:1076, 1990.
Potter & Haley, Meth. in Enzymol., 91, 613-633, 1983.
Queen and Baltimore, *Cell*, 35:741, 1983.
Quinn et al., *Mol. Cell. Biol.*, 9:4713, 1989.
Rakonjac and Model, *J. Mol. Biol.*, 282:25, 1998.
Rakonjac et al., *J. Mol. Biol.*, 289:1253, 1999.
Rao and Torriani, *J Bacteriol.*, 170, 5216, 1988.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ripe et al., *Mol. Cell Biol.*, 9:2224, 1989.
Rittling et al., *Nucl. Acids Res.*, 17:1619, 1989.
Rodi and Makowski, *Curr. Opin. Biotechnol.*, 10:87, 1999.
Rosen et al., *Cell*, 41:813, 1988.
Sakai et al., *Genes and Dev.*, 2:1144, 1988.
Sambrook et al., In: *Molecular Cloning: A Laboratory Manual*, Vol. 1, Cold Spring Harbor Laboratory Press, Cold Spring Harbor, N.Y, Ch. 7,7.19-17.29, 1989.
Sasso et al., *J. Immunol.*, 142:2778-2783, 1989.
Satake et al., *J. Virology*, 62:970, 1988.
Sblattero and Bradbury, *Nat. Biotechnol.*, 18:75, 2000.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sheets et al., *Proc. Natl. Acad. Sci. USA.*, 95:6157, 1998.
Sherman et al., *Mol. Cell. Biol.*, 9:50, 1989.
Shorki et al., J. Immunol., 146:936-940, 1991.
Shusta et al., *J. Mol. Biol.*, 292:949, 1999.
Silvermann et al., *J. Clin. Invest.*, 96:417-426, 1995.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J*, 248:1, 1987.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
T. J. Gibson, PhD thesis, University of Cambridge (1984).
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol Chem.*, 264:15160, 1989.
Thiesen et al., *J. Virology*, 62:614, 1988.
Thompson et al., *J. Mol. Biol.* 256, 77, 1999????.
Thorstenson et al., *J. Bacteriol.*, 179:5333, 1997.
Tomlinson et al., J. Mol. Biol. 227:776, 1992.
Tronche et al., *Mol. Biol. Med.*, 7:173, 1990.
Tronche et al., *Mol. Cell. Biol.*, 9:4759, 1989.
Trudel and Constantini, *Genes and Dev.*, 6:954, 1987.
Tsumaki et al., *J Biol Chem.* 273:22861, 1998.
Van Wielink and Duine, *Trends Biochem Sci.*, 15:136, 1990.
Vannice and Levinson, *J. Virology*, 62:1305, 1988.
Vasseur et al., *Proc. Natl. Acad. Sci. USA.*, 77:1068, 1980.
Vaughan et al., *Nat. Biotechnol.*, 14:309, 1996.
Walker et al., *Nucleic Acids Res.* 20:1691, 1992
Wang and Calame, *Cell*, 47:241, 1986.
Waterhouse et al., Nucl. Acids Res. 21, 2265-2266 (1993)
Watson, M. Nucleic Acids Research, Vol 12, No. 13, 1984, pp. 5145-5164),
Weber et al., *Cell*, 36:983, 1984.
Weinberger et al. *Mol. Cell. Biol.*, 8:988, 1984.
Winoto and Baltimore, *Cell*, 59:649, 1989.
Winter et al, *Ann. Rev. Immunol.* 12: 433, 1994.
Winter et al., *Ann. Rev. Immunol.*, 12:433, 1994.
Wu et al., *Biochem Biophys Res Commun.* 233:221, 1997.
Yutzey et al. *Mol. Cell. Biol.*, 9:1397, 1989.
Zhao-Emonet et al., *Gene Ther.* 6:1638, 1999.

What is claimed is:

1. A method of obtaining a bacterium comprising a nucleic acid sequence encoding a catalytic protein catalyzing a chemical reaction involving a target substrate, the method comprising the steps of:
   (a) providing a Gram negative bacterium comprising a nucleic acid sequence encoding a heterologous candidate catalytic protein, wherein said catalytic protein is expressed in soluble form in the periplasm of said bacterium;
   (b) contacting said bacterium with a target substrate capable of diffusing into said bacterium, wherein said target substrate comprises a molecule containing a scissile amide bond, a scissile carboxylic ester bond, a scissile phosphate ester bond, a scissile sulfonate ester bond, a scissile carbonate ester bond, a scissile carbamate bond, a scissile thioester bond, a nucleic acid, or a polypeptide and said candidate catalytic protein catalyzes a chemical reaction involving said target substrate and wherein said chemical reaction yields at least a first substrate product; and
   (c) selecting said bacterium based on the presence of said first substrate product.

2. The method of claim 1, further defined as a method of obtaining a nucleic acid sequence encoding a catalytic protein catalyzing a reaction with a target substrate, the method further comprising the step of:
   (d) cloning said nucleic acid sequence encoding said candidate catalytic protein.

3. The method of claim 1, wherein said nucleic acid sequence encoding a candidate catalytic protein is further defined as operably linked to a leader sequence capable of directing expression of said candidate catalytic protein in said periplasm.

4. The method of claim 1, wherein said Gram negative bacterium is an *E. coli* bacterium.

5. The method of claim 1, further defined as comprising providing a population of Gram negative bacteria.

6. The method of claim 5, wherein said population of bacteria is further defined as collectively capable of expressing a plurality of candidate catalytic proteins.

7. The method of claim 6, wherein said population of bacteria is obtained by a method comprising the steps of:
   (a) preparing a plurality DNA inserts which collectively encode a plurality of different candidate catalytic proteins, and
   (b) transforming a population of Gram negative bacteria with said DNA inserts.

8. The method of claim 5, wherein said population of Gram negative bacteria is contacted with said target substrate.

9. The method of claim 1, wherein said candidate catalytic protein is further defined as an enzyme.

10. The method of claim 1, wherein said candidate catalytic protein is further defined as not capable of diffusing out of said periplasm.

11. The method of claim 1, wherein said target substrate comprises a molecule containing a scissile amide bond.

12. The method of claim 1, wherein said target substrate comprises a polypeptide.

13. The method of claim 1, wherein said target substrate comprises a molecule containing a scissile carboxylic ester bond.

14. The method of claim 1, wherein said target substrate comprises a nucleic acid.

15. The method of claim 1, wherein said target substrate comprises a molecule containing a scissile phosphate ester bond.

16. The method of claim 1, wherein said target substrate comprises a molecule containing a scissile sulfonate ester bond.

17. The method of claim 1, wherein said target substrate comprises a molecule containing a scissile carbonate ester bond.

18. The method of claim 1, wherein said target substrate comprises a molecule containing a scissile carbamate bond.

19. The method of claim 1, wherein said target substrate comprises a molecule containing a scissile thioester bond.

20. The method of claim 1, wherein said target substrate is further defined as comprising a molecular weight of less than about 20,000 Da.

21. The method of claim 1, wherein said target substrate is further defined as comprising a molecular weight of less than about 5,000 Da.

22. The method of claim 1, wherein said target substrate is further defined as comprising a molecular weight of less than about 3,000 Da.

23. The method of claim 1, wherein said target substrate is further defined as comprising a molecular weight of greater than about 600 Da and less than about 30,000 Da.

24. The method of claim 1, wherein said first substrate product is further defined as capable of being detected based on the presence of a fluorescent signature.

25. The method of claim 24, wherein said fluorescent signature is absent in said target substrate.

26. The method of claim 25, wherein said fluorescent signature is produced by catalytic cleavage of a scissile bond.

27. The method of claim 26, further defined as comprising use of a FRET system, said FRET system comprising a fluorophore bound by a scissile bond to at least a first molecule capable of quenching the fluorescence of said fluorophore, wherein cleavage of said scissile bond allows said first molecule to diffuse away from the fluorophore and wherein the fluorescence of said fluorophore becomes detectable.

28. The method of claim 27, wherein the fluorophore comprises a positive charge allowing the fluorophore to remain associated with the bacterium.

29. The method of claim 24, wherein said target substrate is further defined as comprising a latent fluorescent moiety capable of being released by said chemical reaction involving said target substrate.

30. The method of claim 29, wherein the latent fluorescent moiety released by said cleavage possesses an overall positive charge allowing said moiety to remain associated with the bacterium following said cleavage.

31. The method of claim 24, further defined as comprising labeling said target substrate with a fluorescent pH probe capable of being detected upon a change in pH associated with said chemical reaction involving said target substrate.

32. The method of claim 31, wherein said fluorescent pH probe possesses an overall positive charge allowing said fluorescent pH probe to remain associated with the bacterium following said chemical reaction involving said target substrate.

33. The method of claim 1, wherein said bacterium is further defined as viable following said selecting.

34. The method of claim 1, further comprising treating said bacterium to facilitate said diffusing into said periplasm.

35. The method of claim 34, comprising treating the bacterium with hyperosmotic conditions.

36. The method of claim 34, comprising treating the bacterium with physical stress.

37. The method of claim 34, comprising treating the bacterium with a phage.

38. The method of claim 1, wherein said bacterium is grown at a sub-physiological temperature.

39. The method of claim 38, wherein said sub-physiological temperature is about 25° C.

40. The method of claim 1, wherein said selecting comprises FACS.

41. The method of claim 1, wherein said selecting comprises magnetic separation.

* * * * *

UNITED STATES PATENT AND TRADEMARK OFFICE
CERTIFICATE OF CORRECTION

| | | |
|---|---|---|
| PATENT NO. | : 7,871,796 B2 | Page 1 of 1 |
| APPLICATION NO. | : 11/461757 | |
| DATED | : January 18, 2011 | |
| INVENTOR(S) | : Gang Chen et al. | |

It is certified that error appears in the above-identified patent and that said Letters Patent is hereby corrected as shown below:

In column 1, lines 8-9, delete paragraph and insert
--This invention was made with government support under Grant No. MDA972-97-0009 awarded by the Defense Advanced Research Projects Agency (DARPA). The government has certain rights in the invention.-- therefor.

Signed and Sealed this
Twenty-first Day of June, 2011

David J. Kappos
*Director of the United States Patent and Trademark Office*

SEQUENCE LISTING

<160> NUMBER OF SEQ ID NOS: 22

<210> SEQ ID NO 1
<211> LENGTH: 7
<212> TYPE: PRT
<213> ORGANISM: Mus musculus

<400> SEQUENCE: 1

Gln Thr Thr His Val Pro Pro
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Gln Thr Thr His Val Pro Pro
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Gln Thr Thr His Ser Pro Ala
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Gln Thr Thr His Leu Pro Thr
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Gln Thr Thr His Thr Pro Pro
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

```
<400> SEQUENCE: 6

Gln Thr Thr His Thr Pro Pro
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Gln Thr Thr His Ile Pro Thr
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Gln Thr Thr His Val Pro Pro
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Gln Thr Thr His Val Pro Ala
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Gln Thr Thr His Ile Pro Ala
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Gln Thr Thr His Leu Pro Ala
  1               5

<210> SEQ ID NO 12
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Gln Thr Thr His Val Pro Cys
 1               5

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
caggaaacag ctatgac                                                  17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gaattttctg tatgagg                                                  17

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gccacctccg cctgaacc                                                 18

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ctatgcggcc ccattca                                                  17

<210> SEQ ID NO 17
<211> LENGTH: 351
<212> TYPE: DNA
<213> ORGANISM: Artificial Sequence
<220> FEATURE:
<223> OTHER INFORMATION: Description of Artificial Sequence: Synthetic
      Coding Sequence

<400> SEQUENCE: 17
caggtgcagc tgttgcagtc tgcagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
```

```
agcccgtcct tccaaggcca ggtcaccatc tcagccgaca agtccatcag caccgcctac      240
ctgcagtgga gcagcctgaa ggcctcggac acggccgtgt attactgtgc aagagcttct      300
ccttcggggt tgactattg gggccaaggt accctggtca ccgtctcgag t                351

<210> SEQ ID NO 18
<211> LENGTH: 351
<212> TYPE: DNA
<213> ORGANISM: Artificial Sequence
<220> FEATURE:
<223> OTHER INFORMATION: Description of Artificial Sequence: Synthetic
      Coding Sequence

<400> SEQUENCE: 18
gaggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtgt attactgtgc aagaacgggt     300
tttccggggt tgactattg gggccaaggt accctggtca ccgtctcgag t                351

<210> SEQ ID NO 19
<211> LENGTH: 330
<212> TYPE: DNA
<213> ORGANISM: Artificial Sequence
<220> FEATURE:
<223> OTHER INFORMATION: Description of Artificial Sequence: Synthetic
      Coding Sequence

<400> SEQUENCE: 19
cagtctgtgc tgactcagcc accctcagcg tctgggaccc ccgggcagag ggtcaccatc      60
tcttgttctg gaagcagctc caacatcgga agtaattatg tatactggta ccagcagctc     120
ccaggaacgg cccccaaact cctcatctat aggaataatc agcggccctc agggtccct      180 gaccgattct ctggctccaa gtctggcacc tcagcctccc tggccatcag tgggctccgg     240
tccgaggatg aggctgatta ttactgtgca gcatgggatg acagcctgcg ggctgttgta     300
ttcggcggag ggaccaagct gaccgtccta                                      330

<210> SEQ ID NO 20
<211> LENGTH: 330
<212> TYPE: DNA
<213> ORGANISM: Artificial Sequence
<220> FEATURE:
<223> OTHER INFORMATION: Description of Artificial Sequence: Synthetic
      Coding Sequence

<400> SEQUENCE: 20
cagtctgtgc tgactcagcc accctcagcg tctgggaccc ccgggcagag ggtcaccatc      60
tcttgttctg gaagcagctc caacatcgga agtaattatg tatactggta ccagcagctc     120
ccaggaacgg cccccaaact cctcatctat aggaataatc agcggccctc agggtccct      180 gaccgattct ctggctccaa gtctggcacc tcagcctccc tggccatcag tgggctccgg     240
tccgaggatg aggctgatta ttactgtgca gcatgggatg acagcctggg gggtcctgta     300
ttcggcggag ggaccaagct gaccgtccta                                      330

<210> SEQ ID NO 21
<211> LENGTH: 4
```

-continued

```
<212> TYPE: DNA
<213> ORGANISM: Artificial Sequence
<220> FEATURE:
<223> OTHER INFORMATION: Description of Artificial Sequence: Synthetic
      Coding Sequence

<400> SEQUENCE: 21 ctcg                                                                    4

<210> SEQ ID NO 22
<211> LENGTH: 5
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22 aaaaa                                                                   5
```